(12) United States Patent
Carter et al.

(10) Patent No.: US 6,689,763 B2
(45) Date of Patent: Feb. 10, 2004

(54) ANTIBIOTICS AA-896

(75) Inventors: Guy Thomas Carter, New City, NY (US); Jason Arnold Lotvin, Union, NJ (US); Leonard Alexander McDonald, Mountainside, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 5 days.

(21) Appl. No.: 10/132,005

(22) Filed: Apr. 25, 2002

(65) Prior Publication Data

US 2003/0104986 A1 Jun. 5, 2003

Related U.S. Application Data

(60) Provisional application No. 60/286,402, filed on Apr. 25, 2001, and provisional application No. 60/290,156, filed on May 10, 2001.

(51) Int. Cl.$^7$ .......................... A61K 31/70; C07H 19/06
(52) U.S. Cl. .......................... 514/50; 514/49; 536/28.4; 536/28.53
(58) Field of Search .................. 536/28.4, 28.53; 514/49, 50

(56) References Cited

U.S. PATENT DOCUMENTS 3,674,886 A    7/1972   Lindner et al.

FOREIGN PATENT DOCUMENTS

JP    05078385    2/1991

OTHER PUBLICATIONS

Lin, et al. Muraymycins, Novel Peptidolycan Biosynthesis Inhibitors: Semisynthesis and SAR of Their Derivatives. Bioorganic & Medicinal Chemistry Letters, 2002, vol. 12, pp. 2341–2344.

PCT/US02/13218, International Search Report, Jun. 24, 2003.

Isono, K.; Uramoto, M.; Kusakabe, H.; Kirmura, K.; Izaki, K.; Nelson, C.C.; McCloskey, J.A.; J. Antibiotics, 1985, 38, 1617–1621.

Ubukata, M.; Isono, K.; Kimura, K.; Nelson, C.C.; McCloskey, J.A.; J. Am. Chem. Soc., 1988, 110, 4416–4417.

Kimura, K.; Miyata, N.; Kawanishi, G.; Kamino, Y.; Izaki, K.; Isono, K.; Agric. Biol.Chem, 1989, 53, 1811–1815.

Kimura, K.; Ikeda, Y.; Kagami, S.; Yoshihara, M.; J. Antibiotics, 1998, 51, 1099–1104.

Ubukata, M., Kimura, K.; Isono, K.; Nelson, C.C.; Gregson, J.M.; McClosky, J.A.; J.Org.Chem. 1992, 57, 6392–6403.

English Translation of JP05078385, 2-25-91.

*Primary Examiner*—Kathleen K. Fonda
(74) *Attorney, Agent, or Firm*—Daniel B. Moran

(57) ABSTRACT

This invention relates to new antibiotics designated AA-896-A1, AA-896-A2, AA-896-A3, AA-896-A4, AA-896-A5, AA-896-A6, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-C5, AA-896-D1, AA-896-D2, AA-896-D3 and AA-896-D4 derived from the microorganism Streptomyces spp. LL-AA896 which are useful an anti-bacterial agents.

69 Claims, 22 Drawing Sheets

ANTIBIOTICS AA-896

CROSS REFERENCE TO RELATED APPLICATIONS

"This application claims priority from copending provisional applications Ser. No. 60/286,402 filed on Apr. 25, 2001, Ser. No. 60/290,139, filed on May 10, 2001, Ser. No. 60/286,297 filed Apr. 25, 2001, Ser. No. 60/290,140 filed May 10, 2001, Ser. No. 60/286,402 filed Apr. 25, 2001 and Ser. No. 60/290,156 filed May 10, 2001 the entire disclosures of which are hereby incorporated by reference."

BACKGROUND OF THE INVENTION

1. Field of the Invention

This invention relates to new antibiotics designated AA-896-A1, AA-896-A2, AA-896-A3, AA-896-A4, AA-896-A5, AA896-A6, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-C5, AA-896-D1, AA-896-D2, AA-896-D3, and AA-896-D4 to their production by fermentation, to methods for their recovery and concentration from crude solutions and to processes for their preparation. The present invention includes within its scope the agents in dilute form, as crude concentrates, as a complex of all components and in pure form as individual components. Further, the invention includes novel strains of Streptomyces spp. LL-AA896.

2. Description of the Prior Art

Natural products, Liposidomycins A, B and C, have been isolated and reported to have antibacterial activity(Isono, K.; Uramoto, M.; Kusakabe, H.; Kimura, K.; Izaki, K.; Nelson, C. C.; McCloskey, J. A., *J. Antibiotics*, 1985, 38, 1617–1621. Ubukata, M.; Isono, K.; Kimura, K.; Nelson, C. C.; McCloskey, J. A. *J. Am. Chem. Soc.*, 1988, 110, 4416–4417. Kimura, K.; Miyata, N.; Kawanishi, G.; Kamino, Y.; Izaki, K.; Isono, K. *Agric. Biol. Chem.*, 1989, 53, 1811–1815.). Isolated Liposidomycins A-(I), A-(II), A-(III) and A-(IV) are also reported to have antibacterial activity (Kimura, K.; Ikeda, Y.; Kagami, S.; Yoshihara, M., *J. Antibiotics*, 1998, 51, 1099–1104. and other references herein). The detailed structural analysis of Liposidomycins A, B and C using their chemical degradation products has been reported (Ubukata, M.; Kimura, K.; Isono, K.; Nelson, C. C.; Gregson, J. M.; McClosky, J. A., *J. Org. Chem.*, 1992, 57, 6392–6403). Liposidomycin class compounds are further reported (Patents JP05078385) and are derivatives of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1(2H)-pyrimidinyl)tetrahydro-2-furanyl]propanoic acid or the degraded products of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1(2H)-pyrimidinyl)tetrahydro-2-furanyl]-propanoic acid.

DETAILED DESCRIPTION OF THE INVENTION

Figure 1:
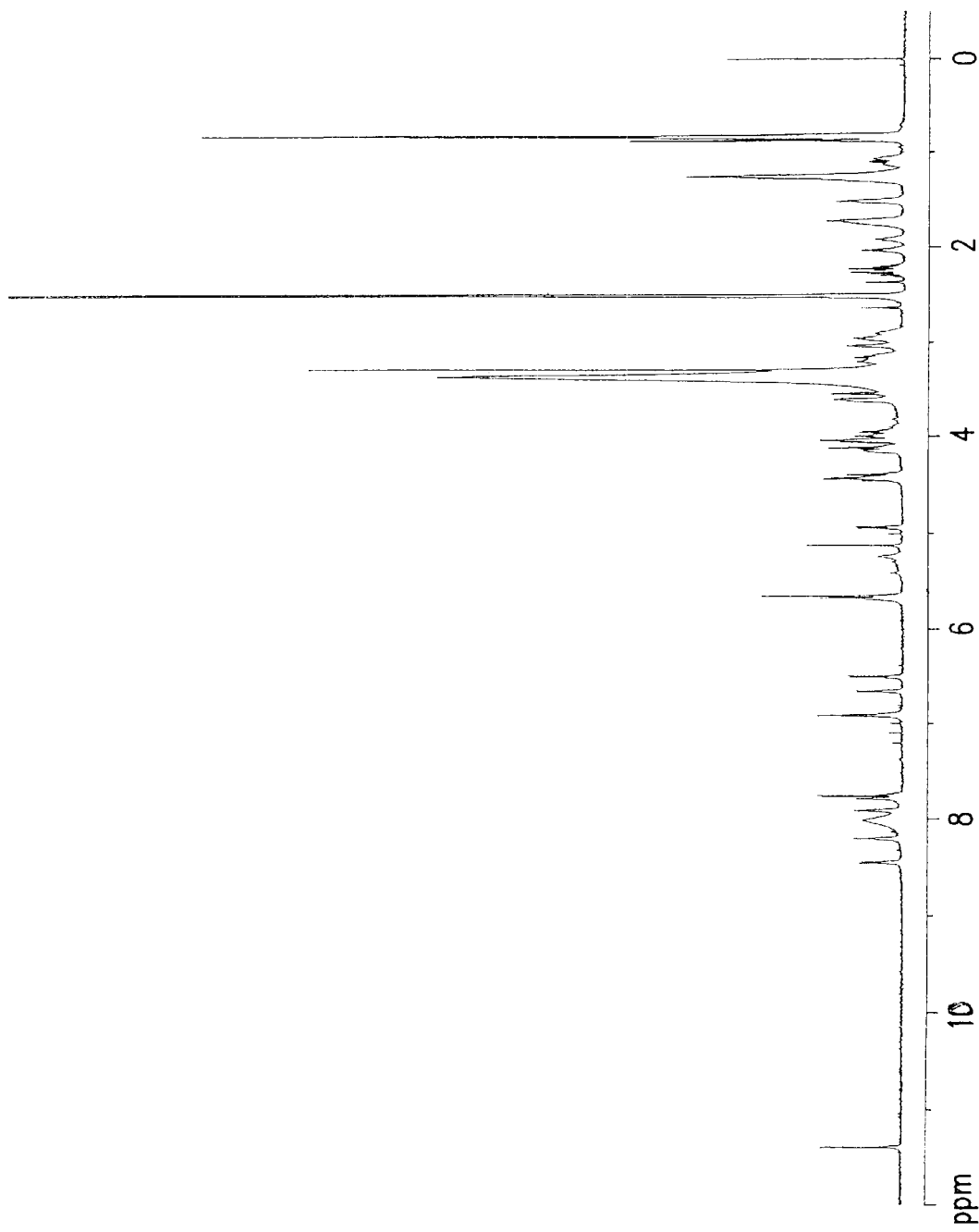
FIG. 1. Proton NMR spectrum of AA-896-B1 in DMSO-$d_6$ at 500 MHz

Compounds according to the invention comprise compounds of the formula:

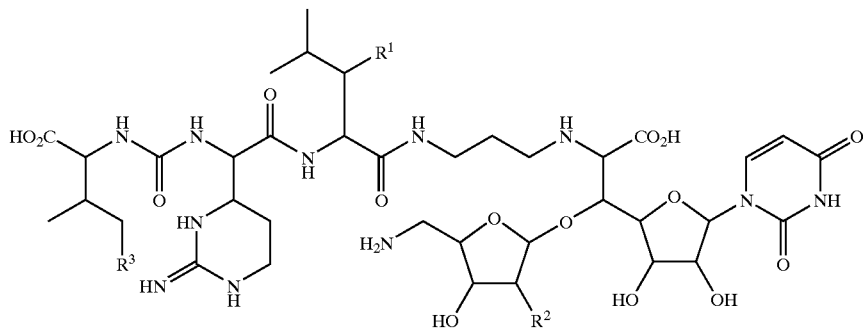

wherein:
$R^1$ is H or $R^4$;
$R^2$ is H, OH or $OCH_3$;
$R^3$ is H or $CH_3$;
$R^4$ is represented by the formula

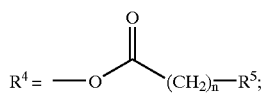

n is an integer from 4 to 12;

$R^5$ is straight and branched alkyl of 1 to 4 carbon atoms, carbamimidoylamino or carbamimidoylhydroxyamino;

or a pharmaceutically acceptable salt thereof.

New antibiotics designated AA-896-A1, AA-896-A2, AA-896-A3, AA-896-A4, AA-896-A5, AA-896-A6, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-C5, AA-896-D1, AA-896-D2, AA-896-D3 and AA-896-D4 have now been found. The structures are:

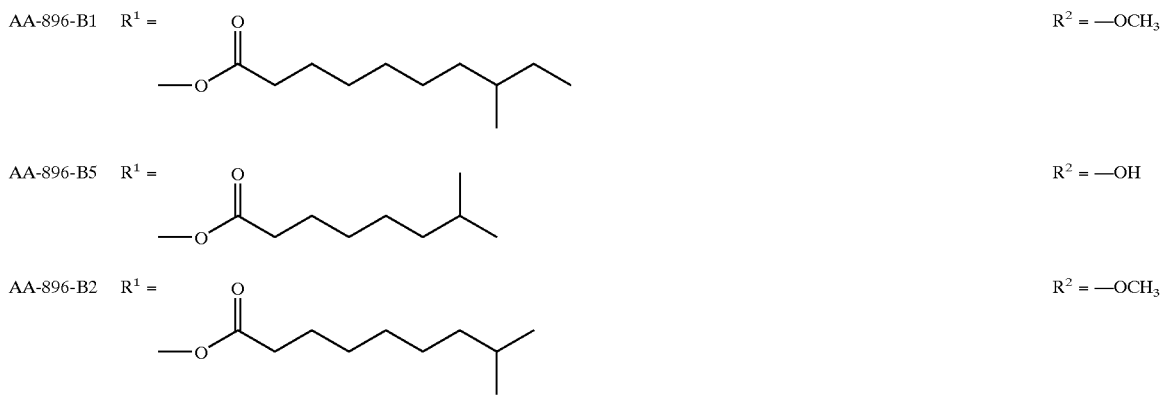

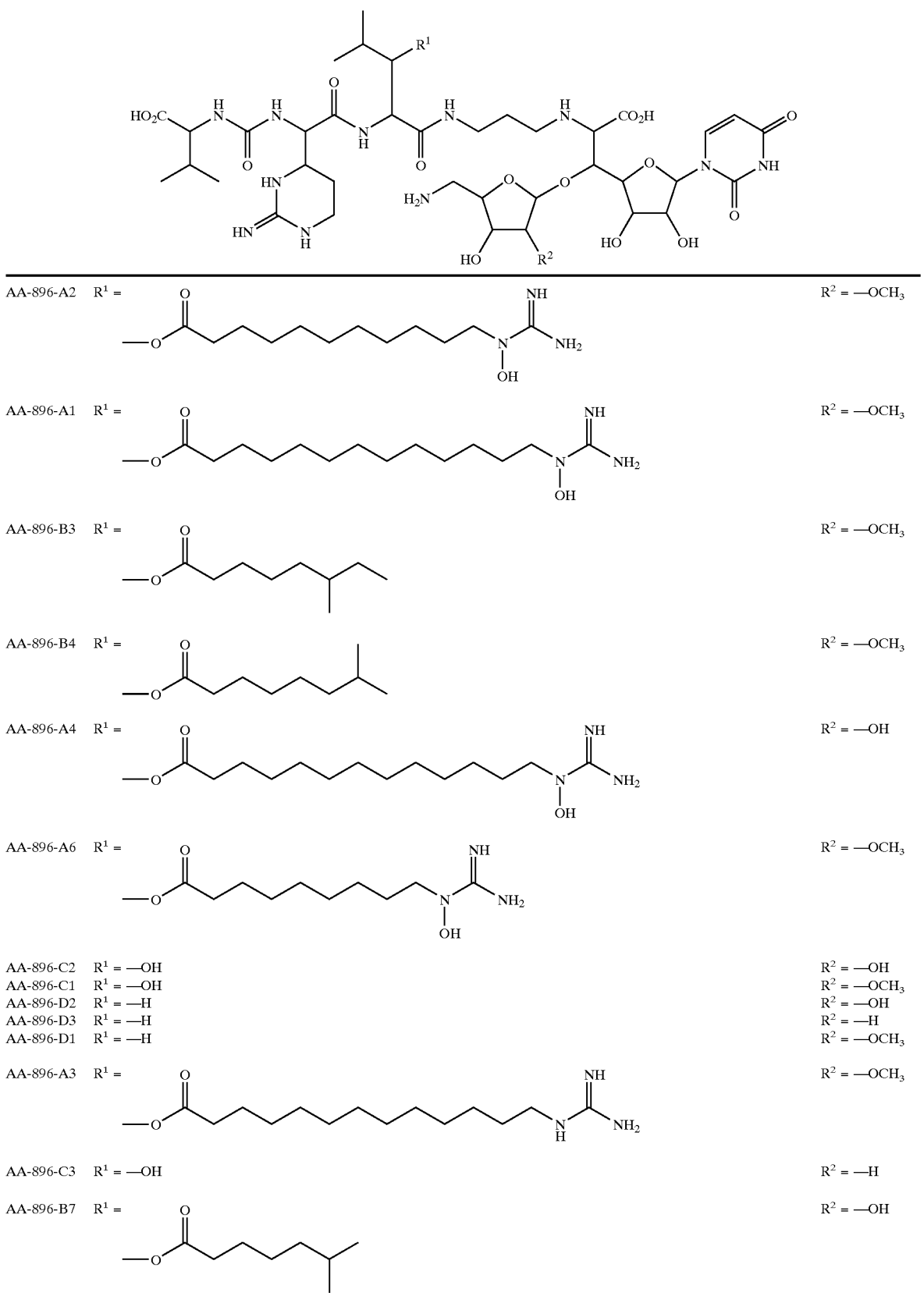

-continued
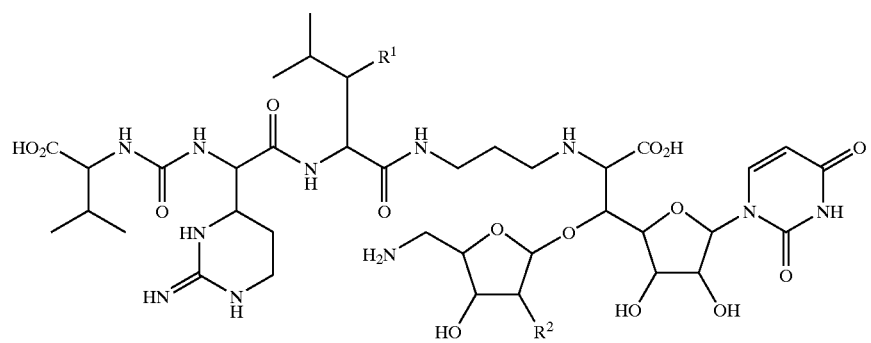
AA-896-B6  R¹ = 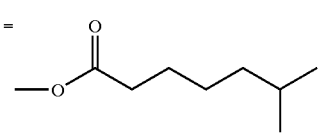  R² = —OCH₃
AA-896-C4
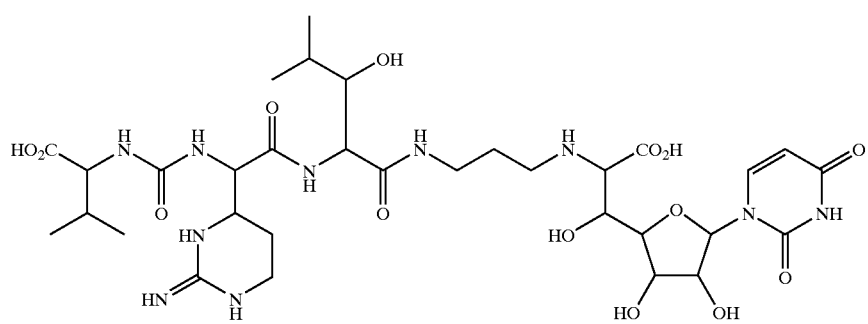
AA-896-A5
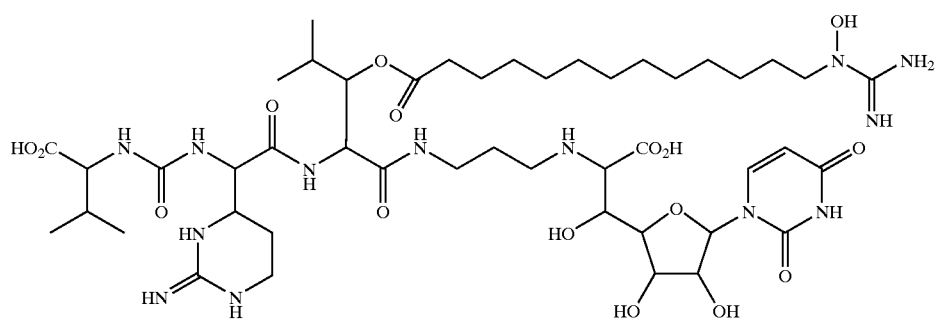
AA896-C5
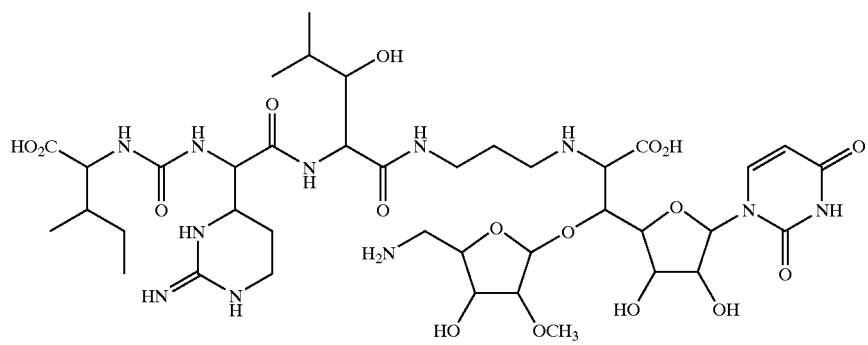

-continued

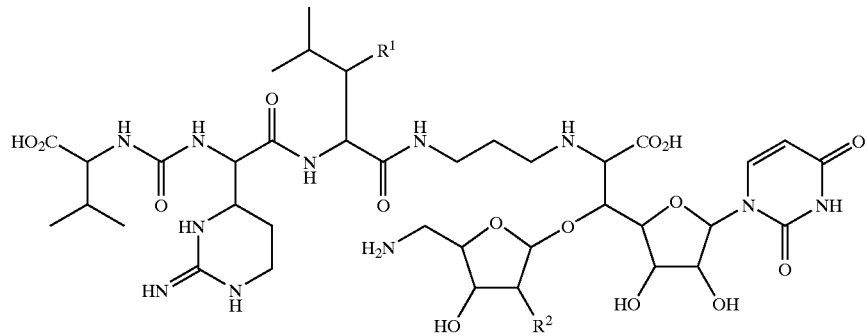

AA-896-D4

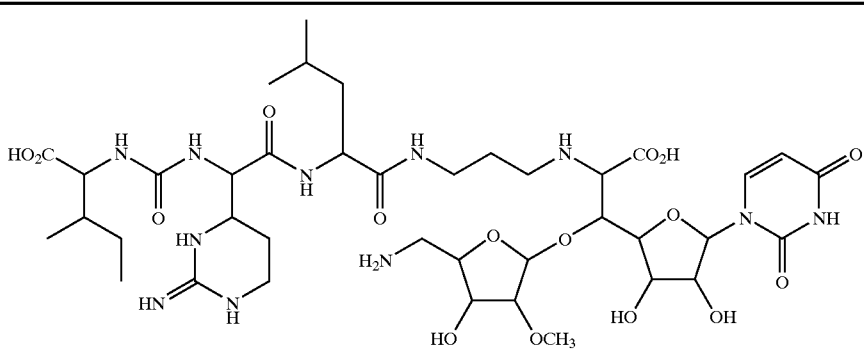

The names of representative AA-896 compounds of the invention are:

| | |
|---|---|
| AA-896-B1 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]]-4-methyl-3-[(8-methyldecanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-B5 | 5-O-[5-Amino-5-deoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-4-methyl-3-[(7-methyloctanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-B2 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-4-methyl-3-[(8-methylnonanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-A2 | 5-O-[5-Amino-5-deoxy-2-O-methyl-β-D-ribofuranosyl]-6-[[3-[3-[[11-(carbamimidoylhydroxy-amino)undecanoyl]oxy]-2-[2-[[(1-carboxy-2-methylpropyl)carbamoyl]amino]-2-(hexahydro-2-iminopyrimidin-4-yl)acetamido]-4-methylpentanamido]propyl]amino]-1,6-dideoxy-1-(3,4-dihydro-2,4-dioxopyrimidin-1(2H)-yl)-β-D-heptof uranuronic acid |
| AA-896-A1 | 5-O-[5-Amino-5-deoxy-2-O-methyl-β-D-ribofuranosyl]-6-[[3-[3-[[13-(carbamimidoylhydroxy-amino)tridecanoyl]oxy]-2-[2-[[(1-carboxy-2-methylpropyl)carbamoyl]amino]-2-(hexahydro-2-iminopyrimidin-4-yl)acetamido]-4-methylpentanamido]propyl]amino]-1,6-dideoxy-1-(3,4-dihydro-2,4-dioxopyrimidin-1(2H)-yl)-β-D-heptofuranuronic acid |
| AA-896-B3 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-4-methyl-3-[(6-methyloctanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-B4 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-4-methyl-3-[(7-methyloctanoyl)oxy]pentanamido]propyl]amino]-1,6-dideoxy-1-(3,4-dihydro-2,4-dioxopyrimidin-1(2H)-yl)-β-D-heptofuranuronic acid |

-continued

| | |
|---|---|
| AA-896-A4 | 5-O-[5-Amino-5-deoxy-β-D-ribofuranosyl]-6-[[3-[3-[[13-(carbamimidoylhydroxyamino)-tridecanoyl]oxy]-2-[2-[[(1-carboxy-2-methylpropyl)carbamoyl]amino]-2-(hexahydro-2-iminopyrimidin-4-yl)acetamido]-4-methylpentanamido]propyl]amino]-1,6-dideoxy-1-(3,4-dihydro-2,4-dioxopyrimidin-1(2H)-yl)-β-D-heptofuranuronic acid |
| AA-896-C2 | 5-O-[5-Amino-5-deoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-3-hydroxy-4-methyl-pentanamido]propyl]amino]-1,6-dideoxy-1-(3,4-dihydro-2,4-dioxopyrimidin-1(2H)-yl)-β-D-heptofuranuronic acid |
| AA-896-C1 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-3-hydroxy-4-methylpentanamido]propyl]amino]-1,6-dideoxy-1-(3,4-dihydro-2,4-dioxopyrimidin-1(2H)-yl)-β-D-heptofuranuronic acid |
| AA-896-D2 | 5-O-[5-Amino-5-deoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-4-methylpentanamido]-propyl]amino]-1,6-dideoxy-1-(3,4-dihydro-2,4-dioxopyrimidin-1(2H)-yl)-β-D-heptofuran-uronic acid |
| AA-896-D3 | 5-O-[5-Amino-2,5-dideoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-4-methylpentanamido]-propyl]amino]-1,6-dideoxy-1-(3,4-dihydro-2,4-dioxopyrimidin-1(2H)-yl)-β-D-heptofuran-uronic acid |
| AA-896-D1 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-4-methyl-pentanamido]propyl]amino]-1,6-dideoxy-1-(3,4-dihydro-2,4-dioxopyrimidin-1(2H)-yl)-β-D-heptofuranuronic acid |
| AA-896-A3 | 5-O-[5-Amino-5-deoxy-2-O-methyl-β-D-ribofuranosyl]-6-[[3-[3-[[13-(carbamimidoylamino)-tridecanoyl]oxy]-2-[2-[[(1-carboxy-2-methylpropyl)carbamoyl]amino]-2-(hexahydro-2-iminopyrimidin-4-yl)acetamido]-4-methylpentanamido]propyl]amino]-1,6-dideoxy-1-(3,4-dihydro-2,4-dioxopyrimidin-1(2H)-yl)-β-D-heptofuranuronic acid |
| AA-896-C3 | 5-O-[5-Amino-2,5-dideoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-3-hydroxy-4-methyl-pentanamido]propyl]amino]-1,6-dideoxy-1-(3,4-dihydro-2,4-dioxopyrimidin-1(2H)-yl)-β-D-heptofuranuronic acid |
| AA-896-B7 | 5-O-[5-Amino-5-deoxy-β-D-ribofuranosyl]-6-[[3-[2-[2-[[(1-carboxy-2-methylpropyl)-carbamoyl]amino]-2-(hexahydro-2-iminopyrimidin-4-yl)acetamido]-4-methyl-3-[(6-methylheptanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-B6 | 5-O-[5-Amino-5-deoxy-2-O-methyl-β-D-ribofuranosyl]-6-[[3-[2-[2-[[(1-carboxy-2-methyl-propyl)carbamoyl]amino]-2-(hexahydro-2-iminopyrimidin-4-yl)acetamido]-4-methyl-3-[(6-methylheptanoyl)oxy]pentanamido]propyl]amino]-1,6-dideoxy-1-(3,4-dihydro-2,4-dioxopyrimidin-1(2H)-yl)-β-D-heptofuranuronic acid |
| AA-896-C4 | 6-[[3-[2-[2-[[(1-Carboxy-2-methylpropyl)carbamoyl]amino]-2-(hexahydro-2-iminopyrimidin-4-yl)acetamido]-3-hydroxy-4-methylpentanamido]propyl]amino]-1,6-dideoxy-1-(3,4-dihydro-2,4-dioxopyrimidin-1(2H)-yl)-β-D-heptofuranuronic acid |
| AA-896-A5 | 6-[[3-[3-[[13-(Carbamimidoylhydroxyamino)tridecanoyl]oxy]-2-[2-[[(1-carboxy-2-methyl-propyl)carbamoyl]amino]-2-(hexahydro-2-iminopyrimidin-4-yl)acetamido]-4-methyl-pentanamido]propyl]amino]-1,6-dideoxy-1-(3,4-dihydro-2,4-dioxopyrimidin-1(2H)-yl)-β-D-heptofuranuronic acid |
| AA-896-C5 | 5-O-[5-Amino-5-deoxy-2-O-methyl-β-D-ribofuranosyl]-6-[[3-[2-[2-[[(1-carboxy-2-methyl-butyl)carbamoyl]amino]-2-(hexahydro-2-iminopyrimidin-4-yl)acetamido]-3-hydroxy-4-methylpentanamido]propyl]amino]-1,6-dideoxy-1-(3,4-dihydro-2,4-dioxopyrimidin-1(2H)-yl)-β-D-heptofuranuronic acid |
| AA-896-D4 | 5-O-[5-Amino-5-deoxy-2-O-methyl-β-D-ribofuranosyl]-6-[[3-[2-[2-[[(1-carboxy-2-methyl-butyl)carbamoyl]amino]-2-(hexahydro-2-iminopyrimidin-4-yl)acetamido]-4-methyl-pentanamido]propyl]amino]-1,6-dideoxy-1-(3,4-dihydro-2,4-dioxopyrimidin-1(2H)-yl)-β-D-heptofuranuronic acid |
| AA-896-A6 | 5-O-[5-Amino-5-deoxy-2-O-methyl-β-D-ribofuranosyl]-6-[[3-[3-[[11-(carbamimidoylhydroxy-amino)nonanoyl]oxy]-2-[2-[[(1-carboxy-2-methylpropyl)carbamoyl]amino]-2-(hexahydro-2-iminopyrimidin-4-yl)acetamido]-4-methylpentanamido]propyl]amino]-1,6-dideoxy-1-(3,4-dihydro-2,4-dioxopyrimidin-1(2H)-yl)-β-D-heptofuranuronicacid |

The physicochemical characteristics of representative examples of the invention are:

AA-896-B1 a) Apparent Molecular Formula: $C_{49}H_{83}N_{11}O_{18}$ b) Molecular Weight: Positive Ion Electrospray MS m/z=1114.3 $(M+H)^+$; 558.0 $(M+2H)^{2+}$; Negative Ion Electrospray MS m/z=1113.3 $(M-H)^-$; High Resolution Fourier Transform MS m/z=1114.6003 $(M+H)^+$ c) Ultraviolet Absorption Spectrum: $\lambda_{max}$ nm (acetonitrile–water)=262
d) Proton Magnetic Resonance Spectrum: (500 MHz DMSO-$d_6$) See FIG. 1.

Figure 2:
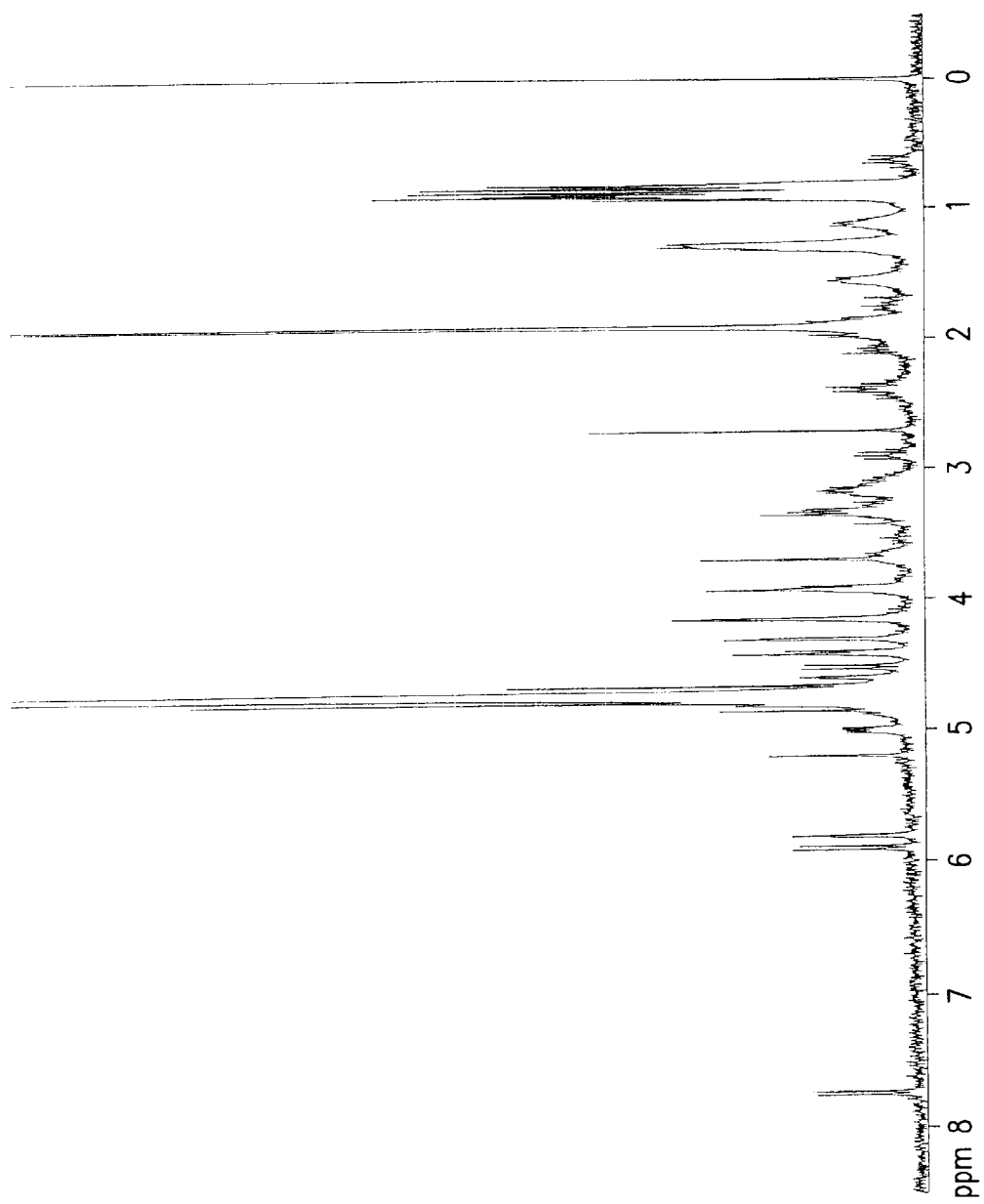
FIG. 2. Proton NMR spectrum of AA-896-B5 in $D_2O$ at 300 MHz

AA-896-B5
a) Apparent Molecular Formula: $C_{46}H_{77}N_{11}O_{18}$
b) Molecular Weight: Positive Ion Electrospray MS m/z= 1072.1 $(M+H)^+$; 536.7 $(M+2H)^{2+}$
c) Ultraviolet Absorption Spectrum: $\lambda_{max}$ nm (acetonitrile-water)=262
d) Proton Magnetic Resonance Spectrum: (300 MHz $D_2O$) See FIG. 2.

Figure 3:
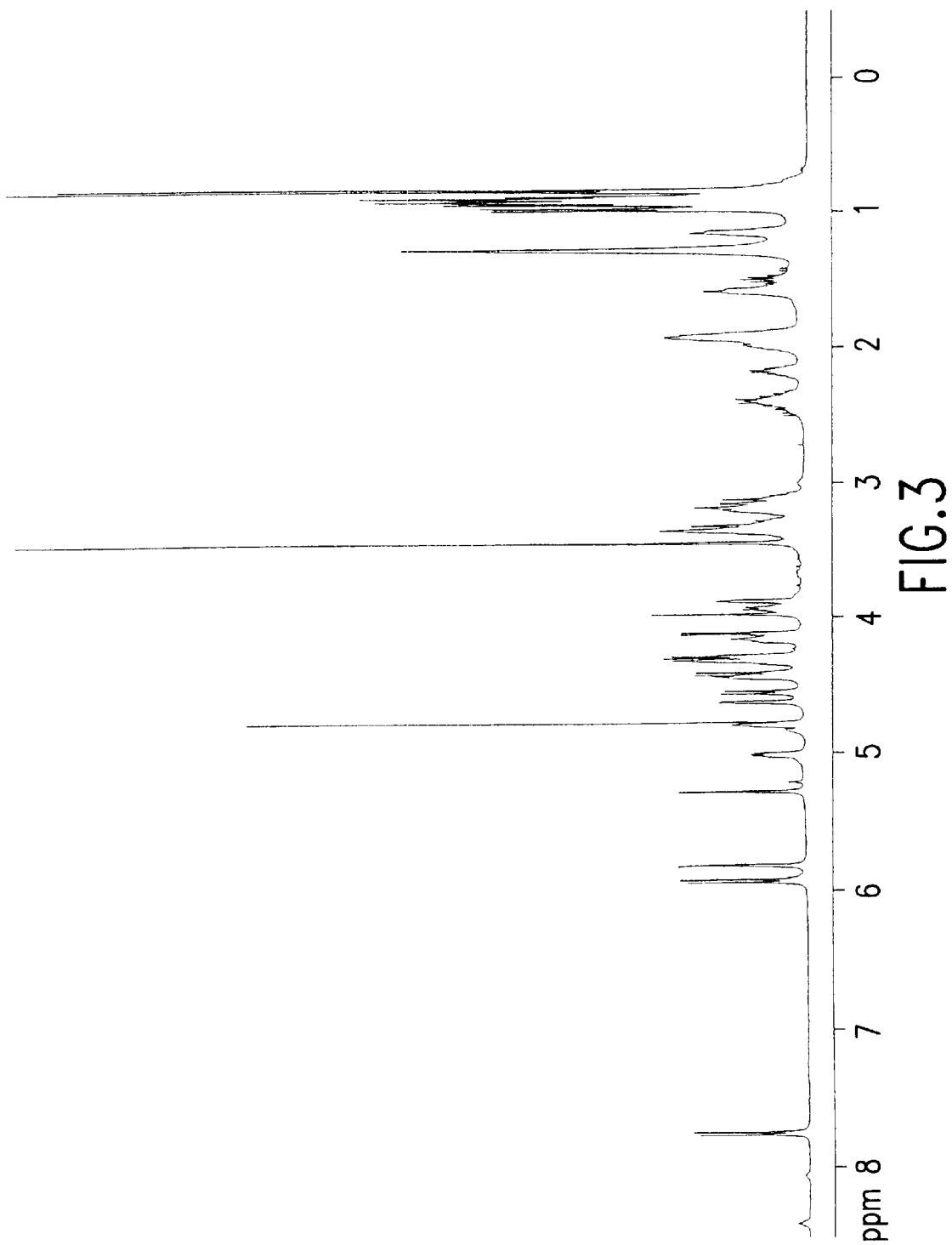
FIG. 3. Proton NMR spectrum of AA-896-B2 in $D_2O$ at 400 MHz

AA-896-B2
a) Apparent Molecular Formula: $C_{48}H_{81}N_{11}O_{18}$
b) Molecular Weight: Positive Ion Electrospray MS m/z= 1100.6 $(M+H)^+$; 550.8 $(M+2H)^{2+}$; Negative Ion Electrospray MS m/z=1098.5 $(M-H)^-$; High Resolution Fast Atom Bombardment MS m/z=1100.5881 $(M+H)^+$
c) Ultraviolet Absorption Spectrum: $\lambda_{max}$ nm (acetonitrile-water)=262
d) Proton Magnetic Resonance Spectrum: (400 MHz $D_2O$) See FIG. 3.

Figure 4:
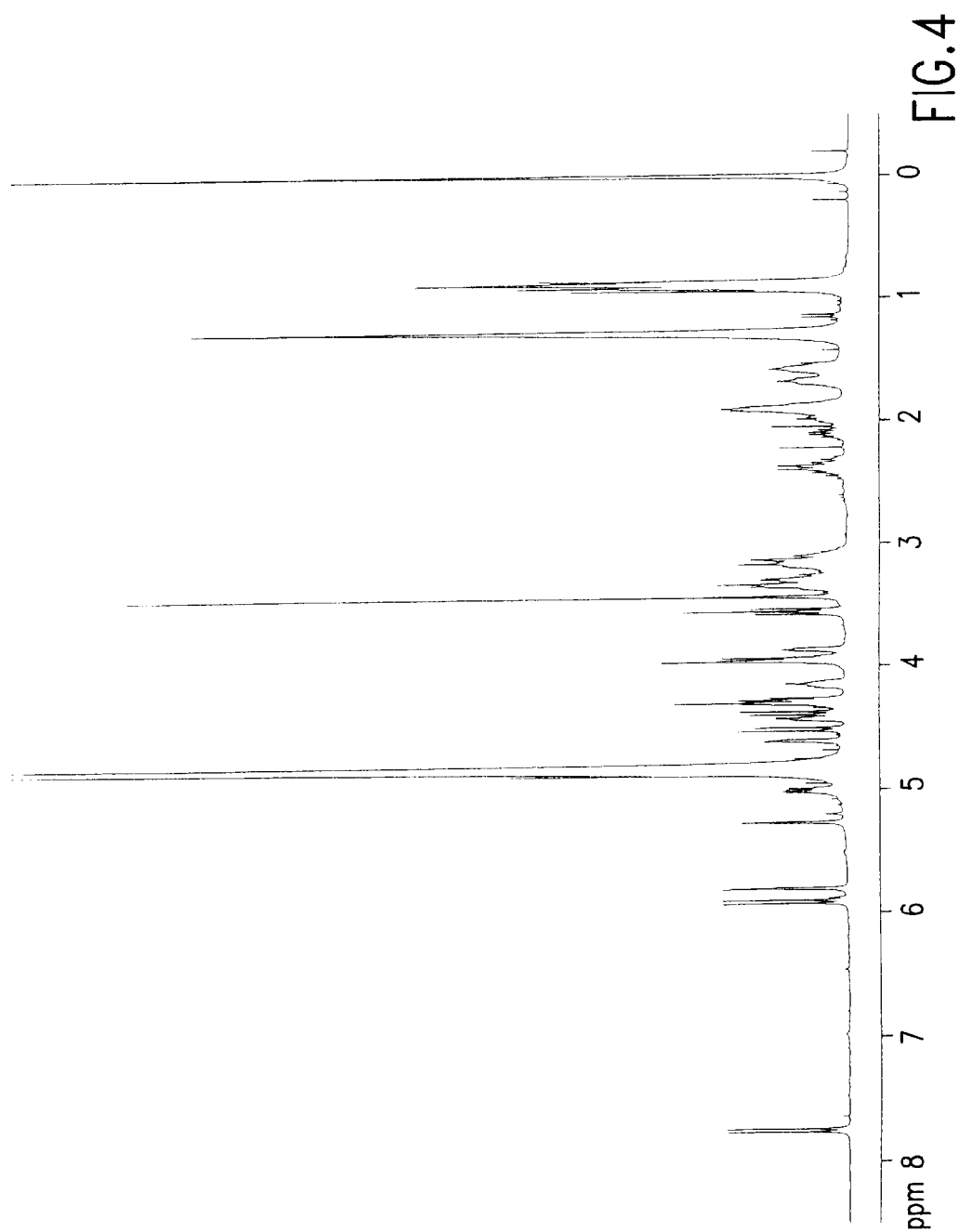
FIG. 4. Proton NMR spectrum of AA-896-A2 in $D_2O$ at 300 MHz

AA-896-A2
a) Apparent Molecular Formula: $C_{50}H_{86}N_{14}O_{19}$
b) Molecular Weight: Positive Ion Electrospray MS m/z= 1187.7 $(M+H)^+$; 594.3 $(M+2H)^{2+}$; Negative Ion Electrospray MS m/z=1185.7 $(M-H)^-$; High Resolution Fast Atom Bombardment MS m/z=1187.6334 $(M+H)^+$
c) Ultraviolet Absorption Spectrum: $\lambda_{max}$ nm (acetonitrile-water)=262
d) Proton Magnetic Resonance Spectrum: (300 MHz $D_2O$) See FIG. 4.

Figure 5:
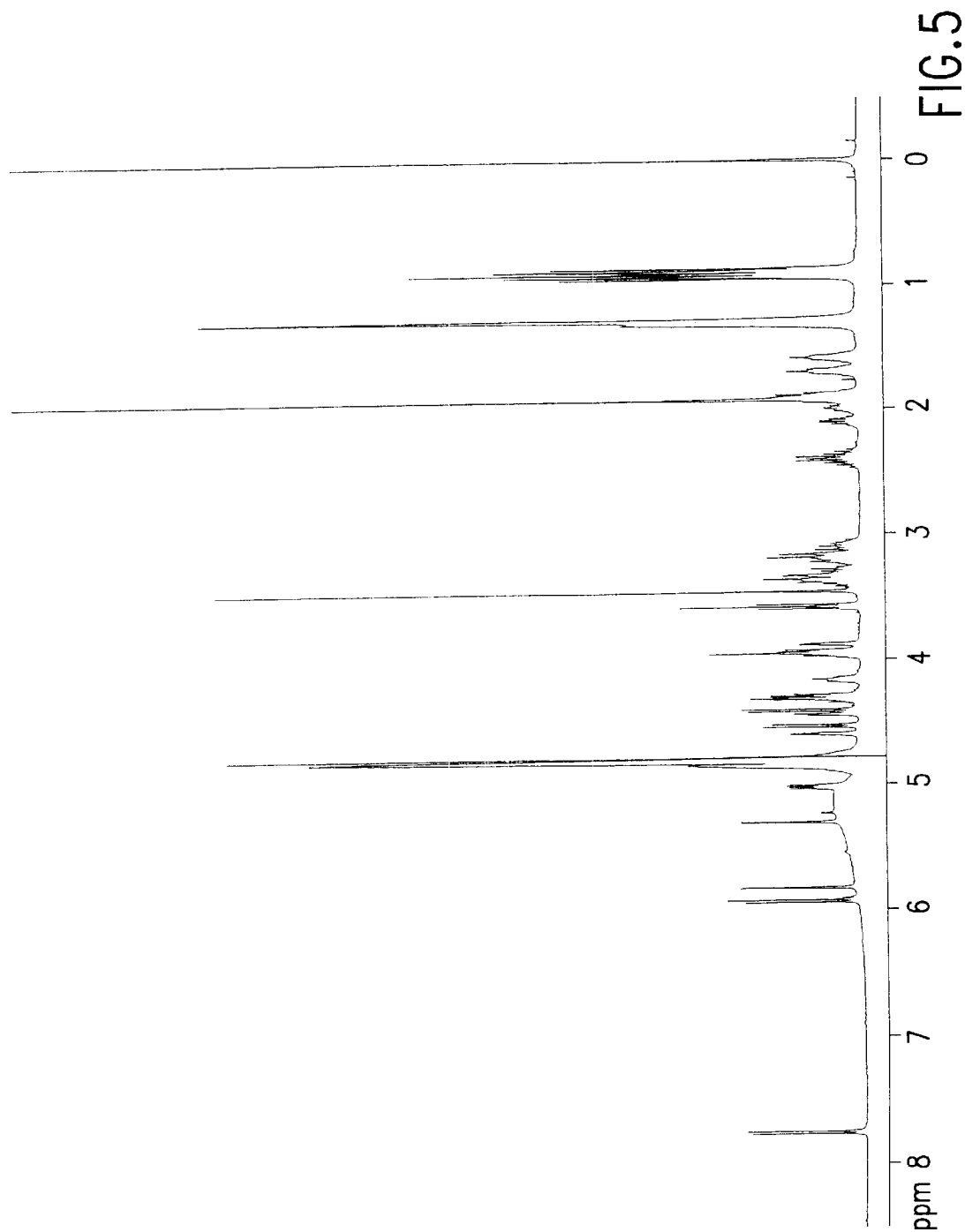
FIG. 5. Proton NMR spectrum of AA-896-A1 in $D_2O$ at 400 MHz

AA-896-A1
a) Apparent Molecular Formula: $C_{52}H_{90}N_{14}O_{19}$
b) Molecular Weight: Positive Ion Electrospray MS m/z= 1215.9 $(M+H)^+$; 608.3 $(M+2H)^{2+}$; High Resolution Fourier Transform MS m/z=1215.6391 $(M+H)^+$
c) Ultraviolet Absorption Spectrum: $\lambda_{max}$ nm (acetonitrile-water)=262
d) Proton Magnetic Resonance Spectrum: (400 MHz $D_2O$) See FIG. 5.

Figure 6:
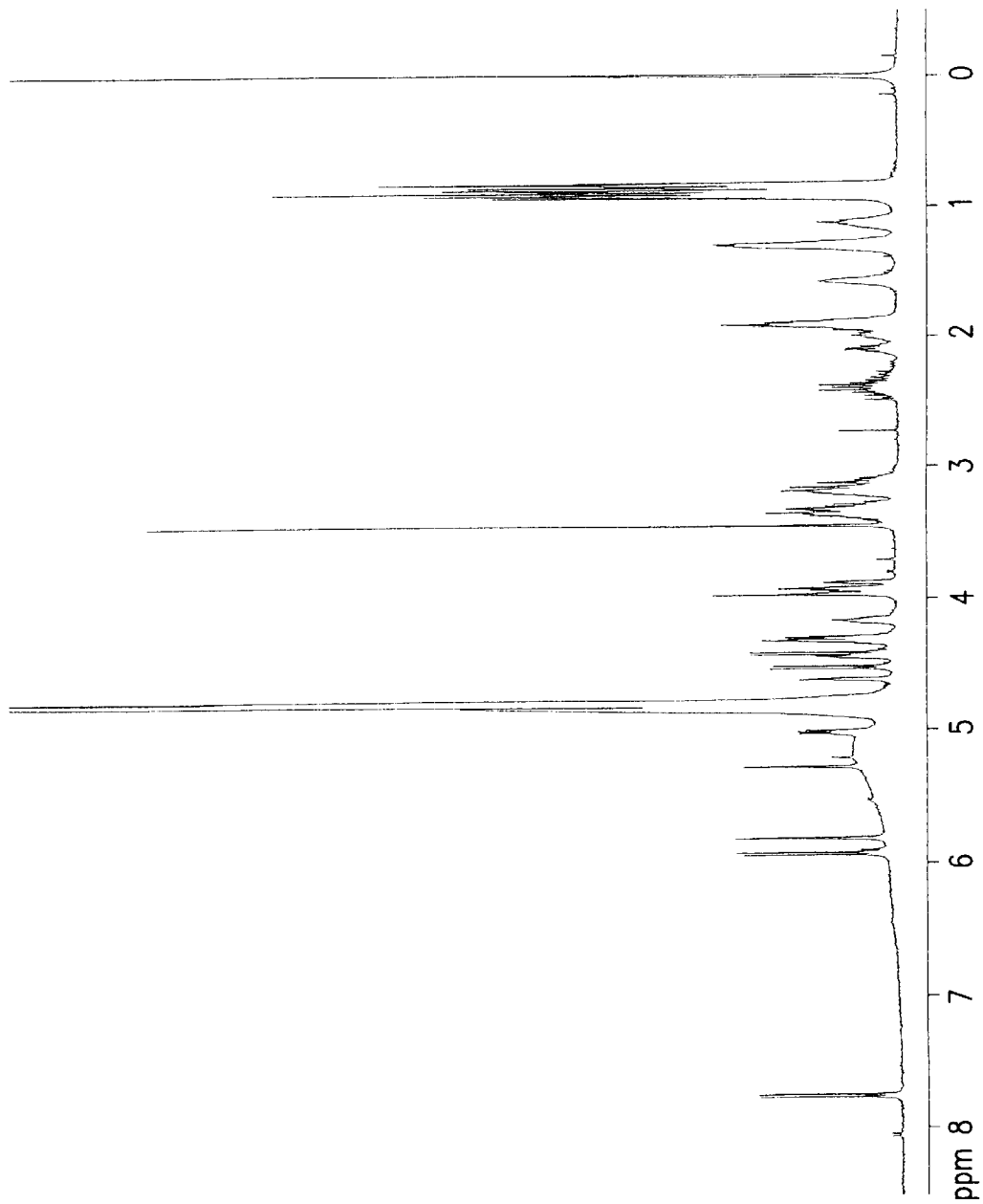
FIG. 6. Proton NMR spectrum of AA-896-B3 in $D_2O$ at 400 MHz

AA-896-B3
a) Apparent Molecular Formula: $C_{47}H_{79}N_{11}O_{18}$
b) Molecular Weight: Positive Ion Electrospray MS m/z= 1086.5 $(M+H)^+$; 543.8 $(M+2H)^{2+}$; Negative Ion Electrospray MS m/z=1084.3 $(M-H)^-$
c) Ultraviolet Absorption Spectrum: $\lambda_{max}$ nm (acetonitrile-water)=262
d) Proton Magnetic Resonance Spectrum: (400 MHz $D_2O$) See FIG. 6.

Figure 7:
FIG. 7. Proton NMR spectrum of AA-896-B4 in $D_2O$ at 300 MHz

AA-896-B4
a) Apparent Molecular Formula: $C_{47}H_{79}N_{11}O_{18}$
b) Molecular Weight: Positive Ion Electrospray MS m/z= 1086.6 $(M+H)^+$; 543.9 $(M+2H)^{2+}$; Negative Ion Electrospray MS m/z=1084.6 $(M-H)^-$
c) Ultraviolet Absorption Spectrum: $\lambda_{max}$ nm (acetonitrile-water)=262
d) Proton Magnetic Resonance Spectrum: (300 MHz $D_2O$) See FIG. 7.

Figure 8:
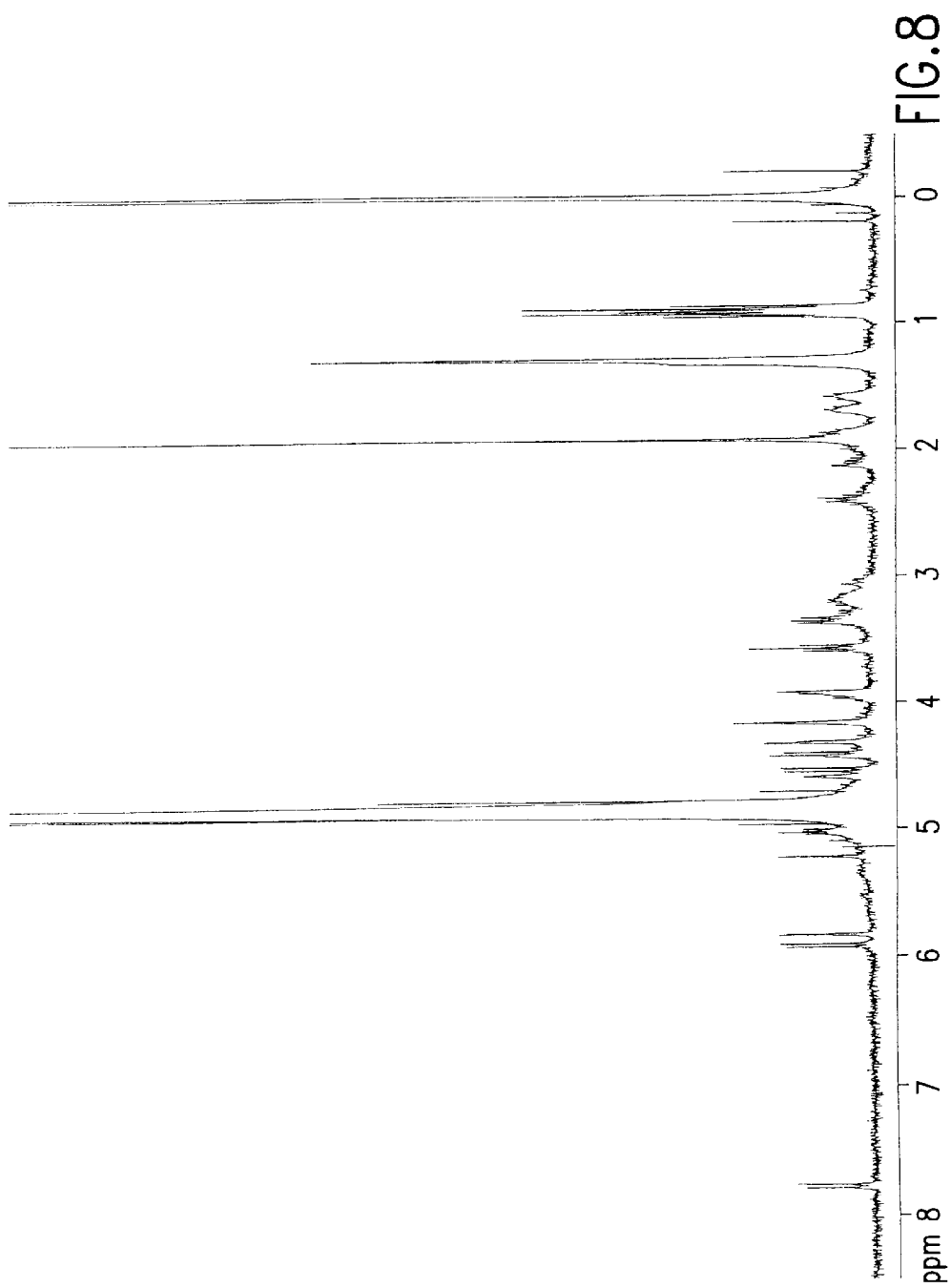
FIG. 8. Proton NMR spectrum of AA-896-A4 in $D_2O$ at 300 MHz

AA-896-A4
a) Apparent Molecular Formula: $C_{51}H_{88}N_{14}O_{19}$
b) Molecular Weight: Positive Ion Electrospray MS m/z= 1201.7 $(M+H)^+$; 601.4 $(M+2H)^{2+}$; Negative Ion Electrospray MS m/z=1199.6 $(M-H)^-$ c) Ultraviolet Absorption Spectrum: $\lambda_{max}$ nm (acetonitrile-water)=262
d) Proton Magnetic Resonance Spectrum: (300 MHz $D_2O$) See FIG. 8.

Figure 9:
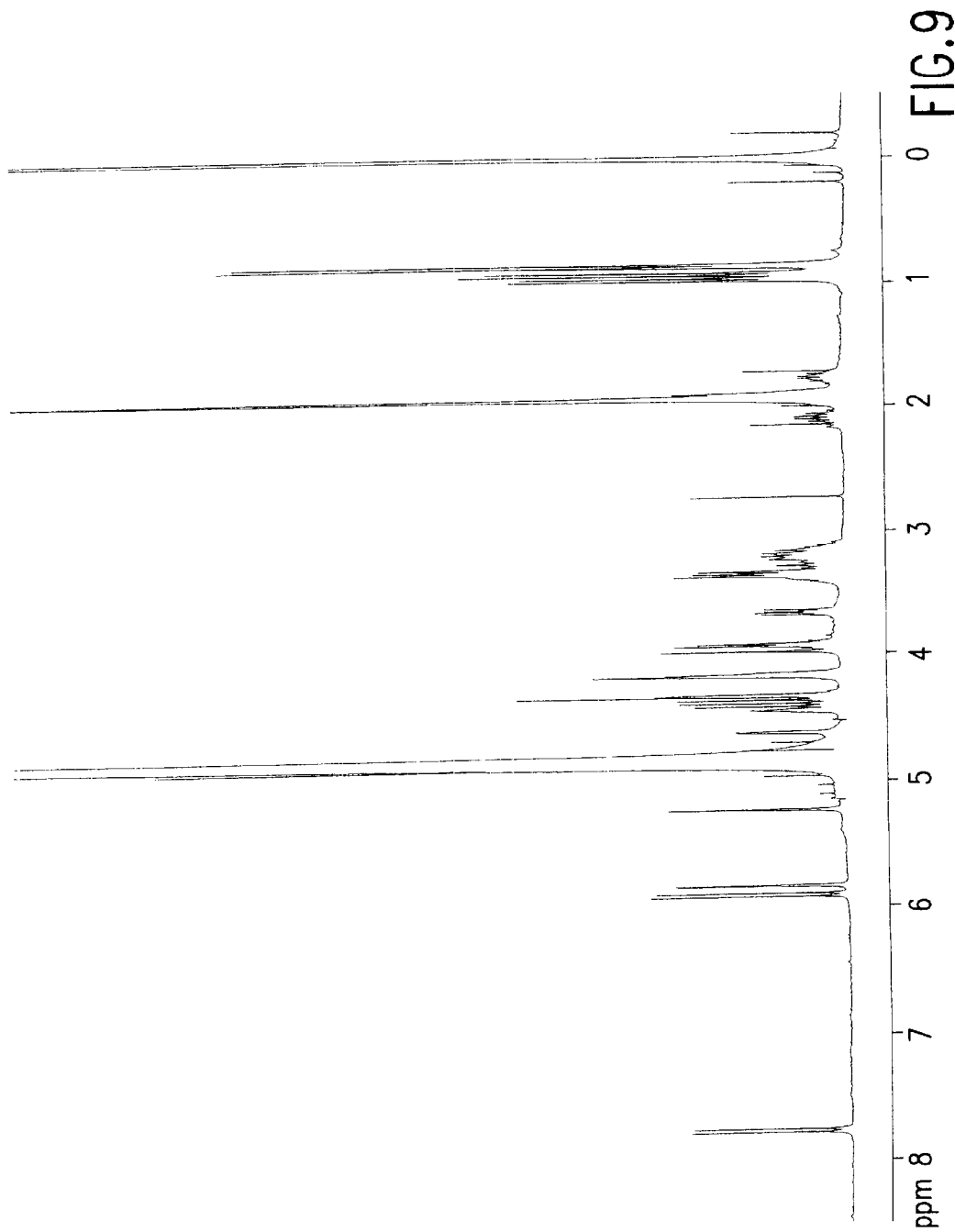
FIG. 9. Proton NMR spectrum of AA-896-C2 in $D_2O$ at 300 MHz

AA-896-C2
a) Apparent Molecular Formula: $C_{37}H_{61}N_{11}O_{17}$
b) Molecular Weight: Positive Ion Electrospray MS m/z= 932.2 $(M+H)^+$; 466.6 $(M+2H)^{2+}$; Negative Ion Electrospray MS m/z=930.2 $(M-H)^-$
c) Ultraviolet Absorption Spectrum: $\lambda_{max}$ nm (acetonitrile-water)=262
d) Proton Magnetic Resonance Spectrum: (300 MHz $D_2O$) See FIG. 9.

Figure 10:
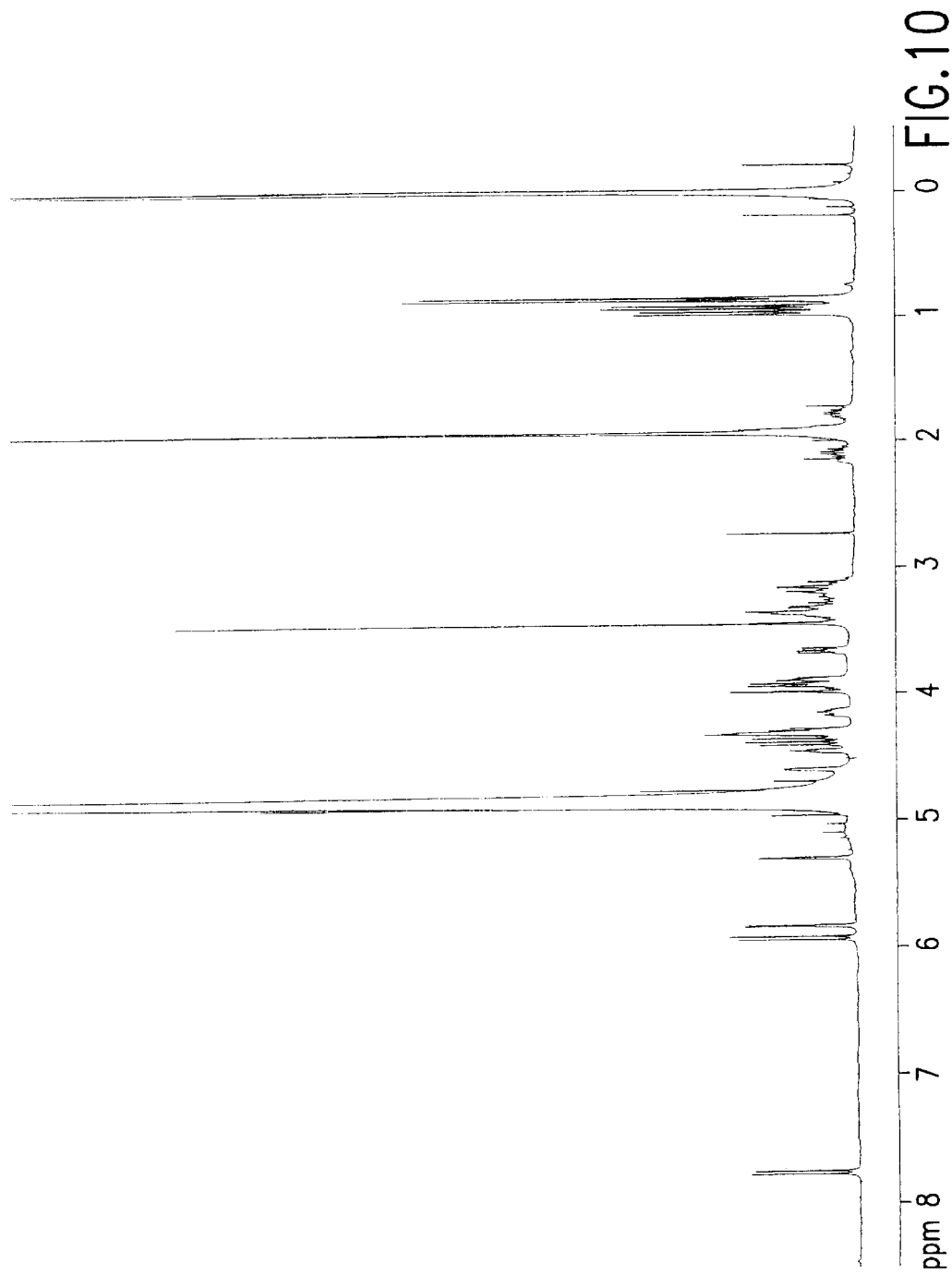
FIG. 10. Proton NMR spectrum of AA-896-C1 in $D_2O$ at 300 MHz

AA-896-C1
a) Apparent Molecular Formula: $C_{38}H_{63}N_{11}O_{17}$
b) Molecular Weight: Positive Ion Electrospray MS m/z= 946.3 $(M+H)^+$; 473.6 $(M+2H)^{2+}$; Negative Ion Electrospray MS m/z=944.2 $(M-H)^-$
c) Ultraviolet Absorption Spectrum: $\lambda_{max}$ nm (acetonitrile-water)=262
d) Proton Magnetic Resonance Spectrum: (300 MHz $D_2O$) See FIG. 10.

Figure 11:
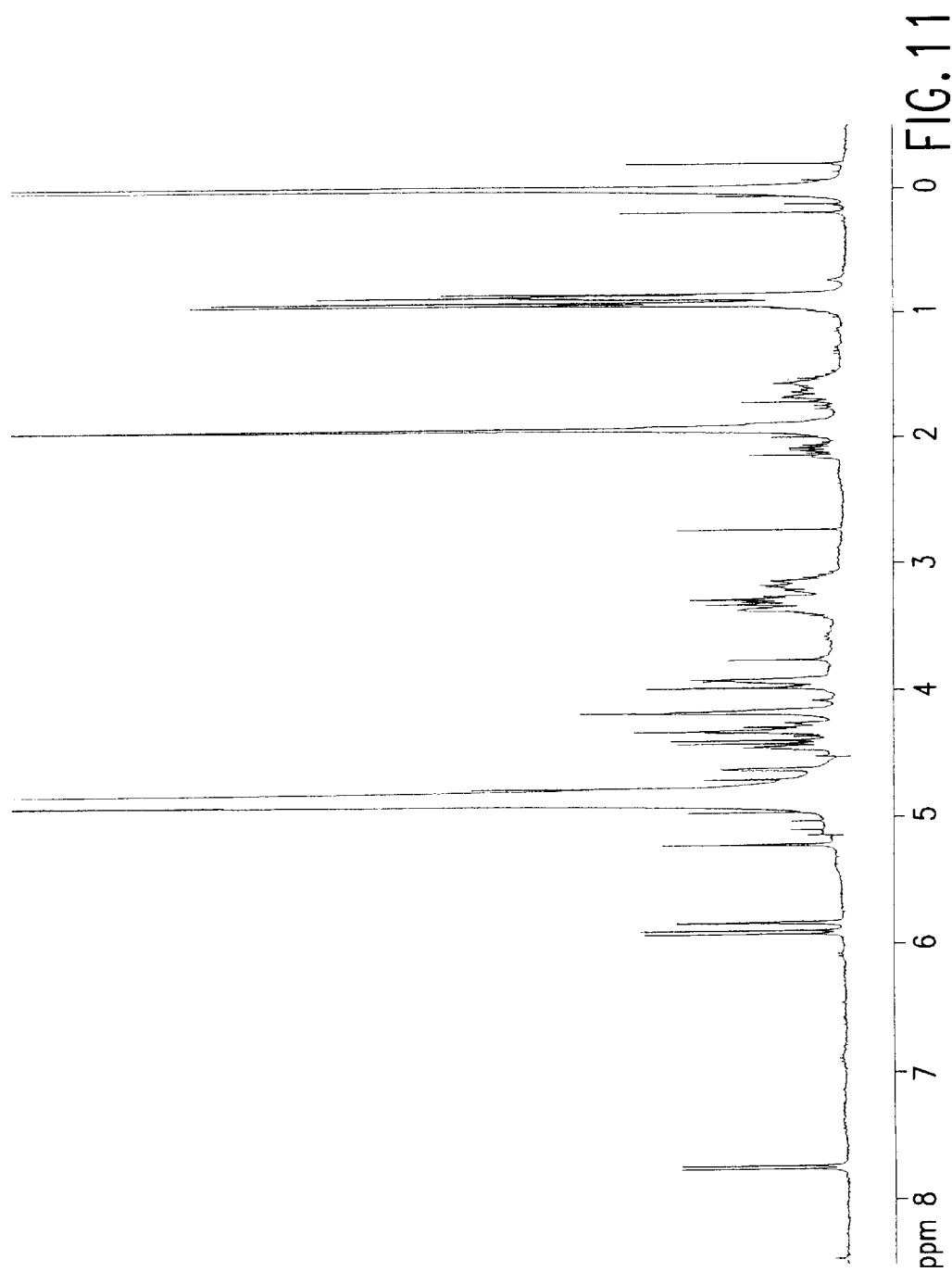
FIG. 11. Proton NMR spectrum of AA-896-D2 in $D_2O$ at 300 MHz

AA-896-D2
a) Apparent Molecular Formula: $C_{37}H_{61}N_{11}O_{16}$
b) Molecular Weight: Positive Ion Electrospray MS m/z= 916.3 $(M+H)^+$; 458.6 $(M+2H)^{2+}$; Negative Ion Electrospray MS m/z=914.2 $(M-H)^-$
c) Ultraviolet Absorption Spectrum: $\lambda_{max}$ nm (acetonitrile-water)=262
d) Proton Magnetic Resonance Spectrum: (300 MHz $D_2O$) See FIG. 11.

Figure 12:
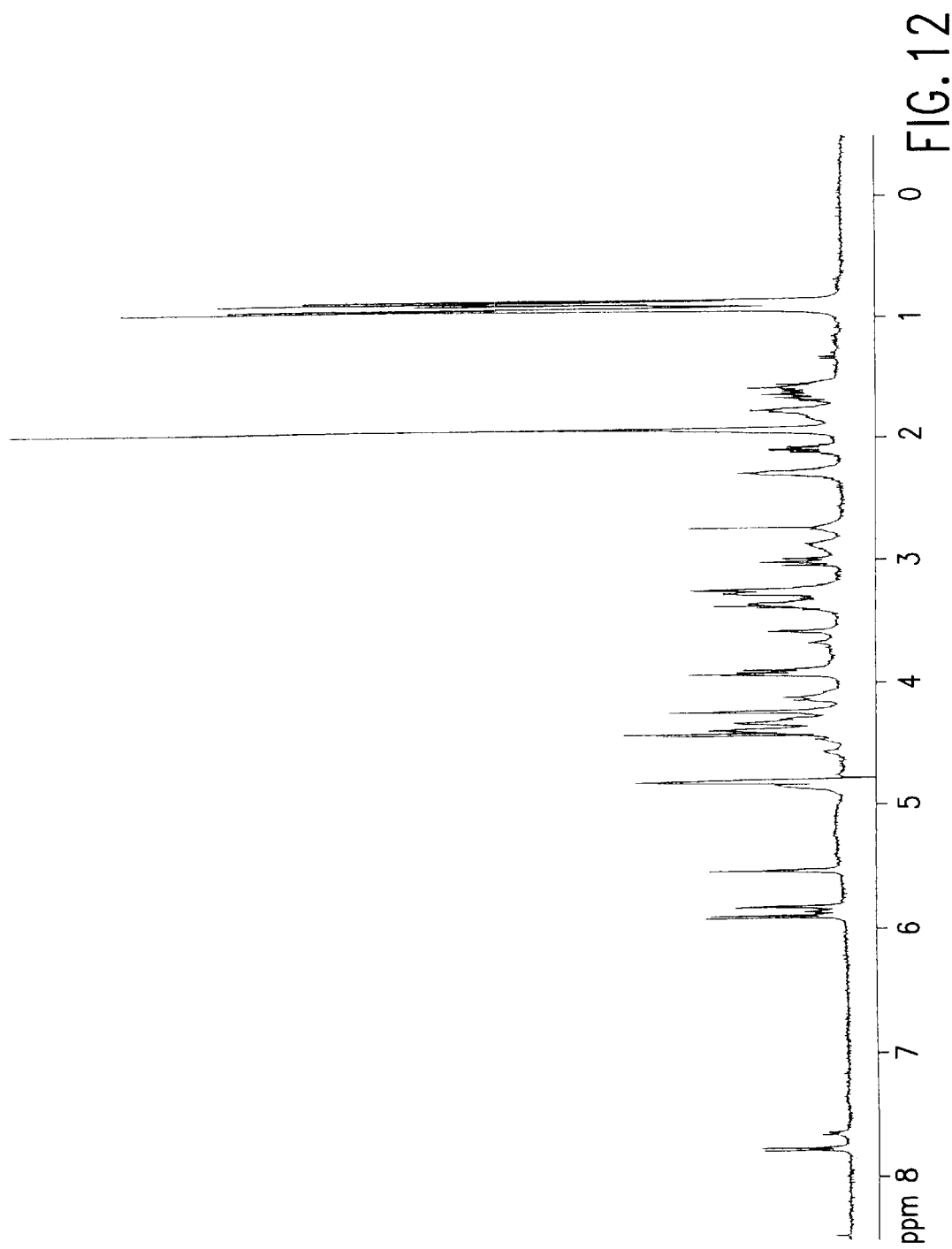
FIG. 12. Proton NMR spectrum of AA-896-D3 in $D_2O$ at 400 MHz

AA-896-D3
a) Apparent Molecular Formula: $C_{37}H_{61}N_{11}O_{15}$
b) Molecular Weight: Positive Ion Electrospray MS m/z= 900.3 $(M+H)^+$; 450.7 $(M+2H)^{2+}$; Negative Ion Electrospray MS m/z=898.3 $(M-H)^-$
c) Ultraviolet Absorption Spectrum: $\lambda_{max}$ nm (acetonitrile-water)=262
d) Proton Magnetic Resonance Spectrum: (400 MHz $D_2O$) See FIG. 12.

Figure 13:
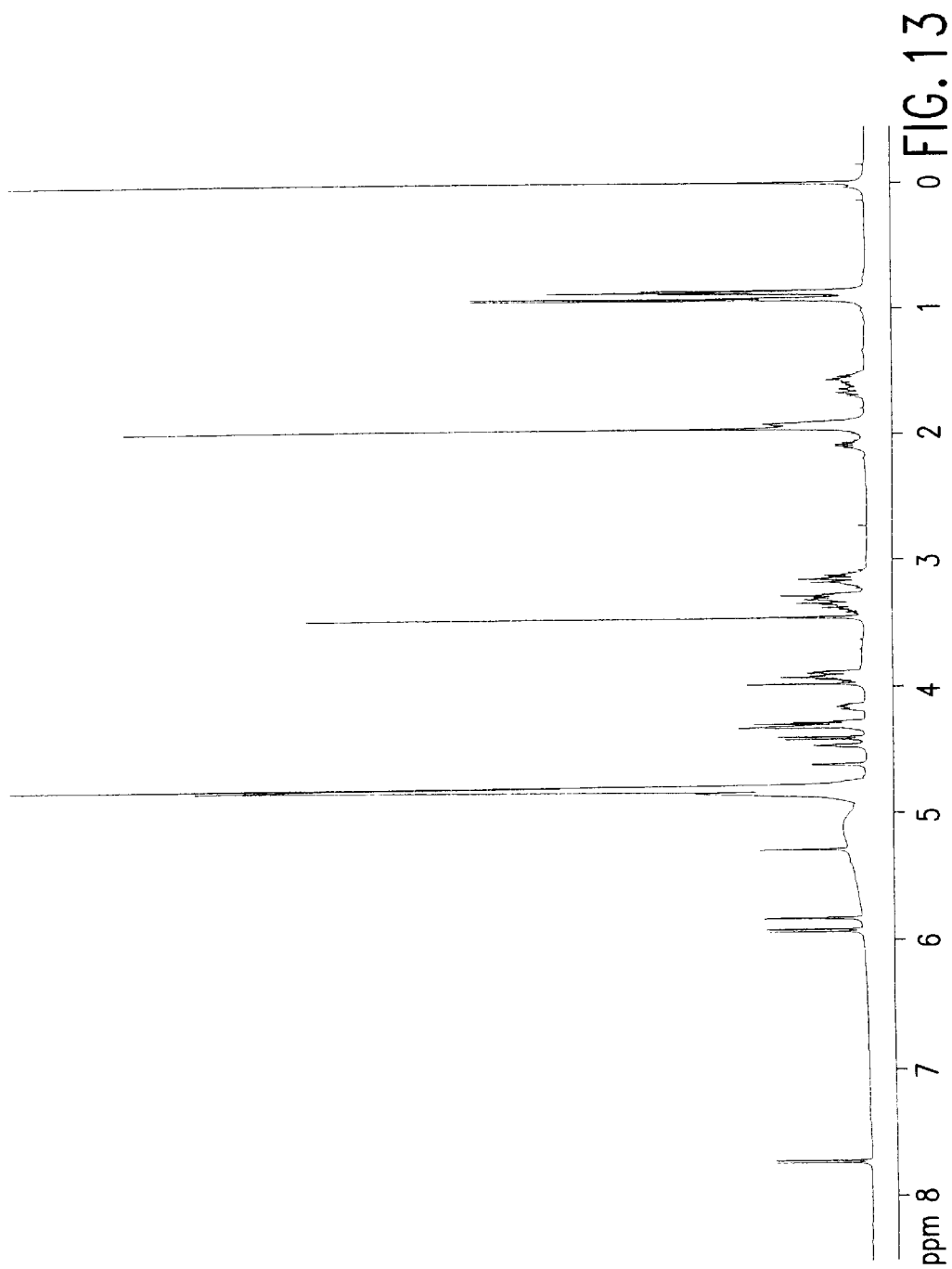
FIG. 13. Proton NMR spectrum of AA-896-D1 in $D_2O$ at 400 MHz

AA-896-D1
a) Apparent Molecular Formula: $C_{38}H_{63}N_{11}O_{16}$
b) Molecular Weight: Positive Ion Electrospray MS m/z= 930.3 $(M+H)^+$; 465.7 $(M+2H)^{2+}$; Negative Ion Electrospray MS m/z=928.4 $(M-H)^-$
c) Ultraviolet Absorption Spectrum: $\lambda_{max}$ nm (acetonitrile-water)=262
d) Proton Magnetic Resonance Spectrum: (400 MHz $D_2O$) See FIG. 13.

Figure 14:
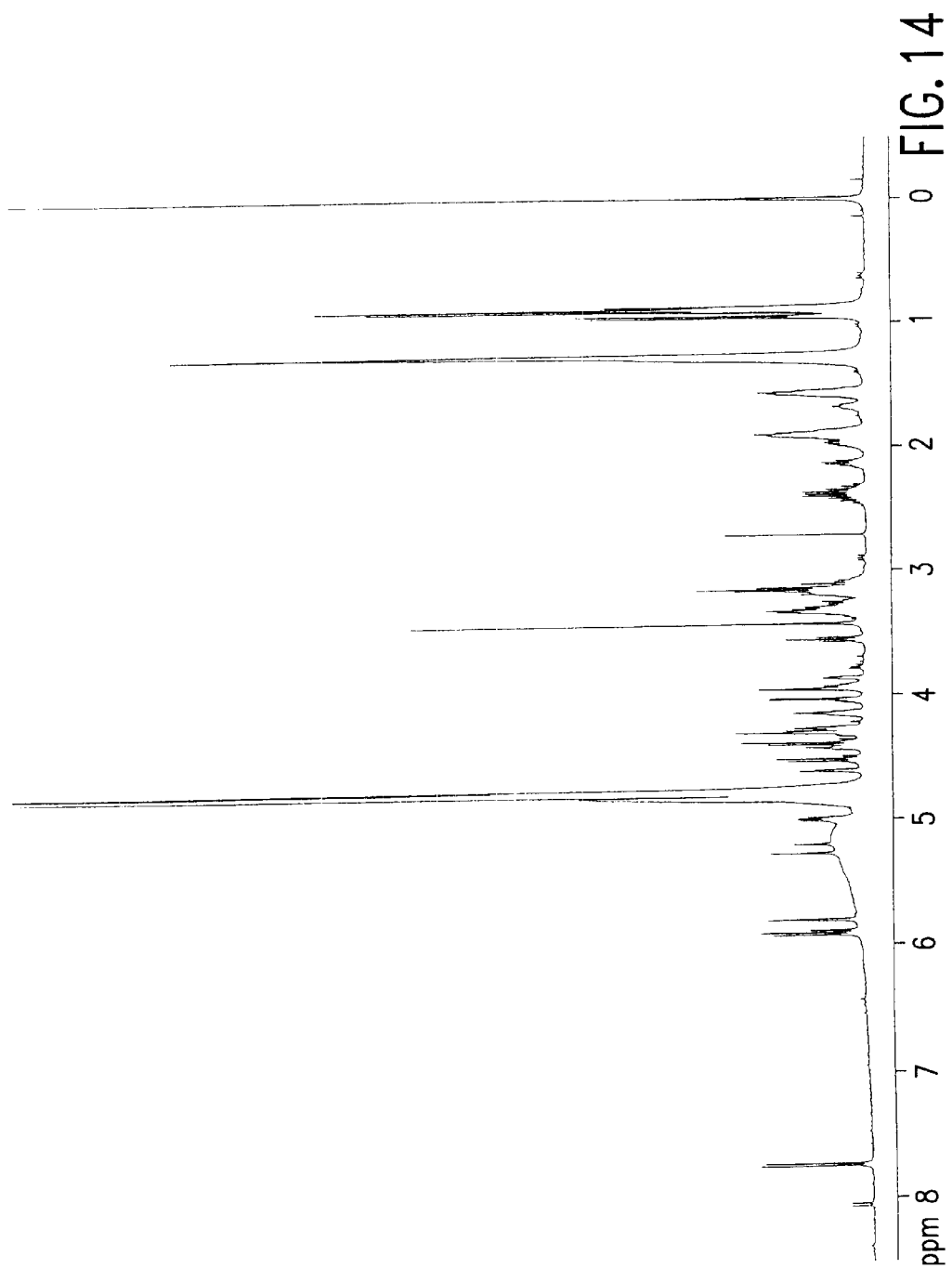
FIG. 14. Proton NMR spectrum of AA-896-A3 in $D_2O$ at 400 MHz

AA-896-A3
a) Apparent Molecular Formula: $C_{52}H_{90}N_{11}O_{18}$
b) Molecular Weight: Positive Ion Electrospray MS m/z= 1199.7 $(M+H)^+$; 600.2 $(M+2H)^{2+}$; Negative Ion Electrospray MS m/z=1197.6 $(M-H)^-$
c) Ultraviolet Absorption Spectrum: $\lambda_{max}$ nm (acetonitrile-water)=262
d) Proton Magnetic Resonance Spectrum: (400 MHz $D_2O$) See FIG. 14.

Figure 15:
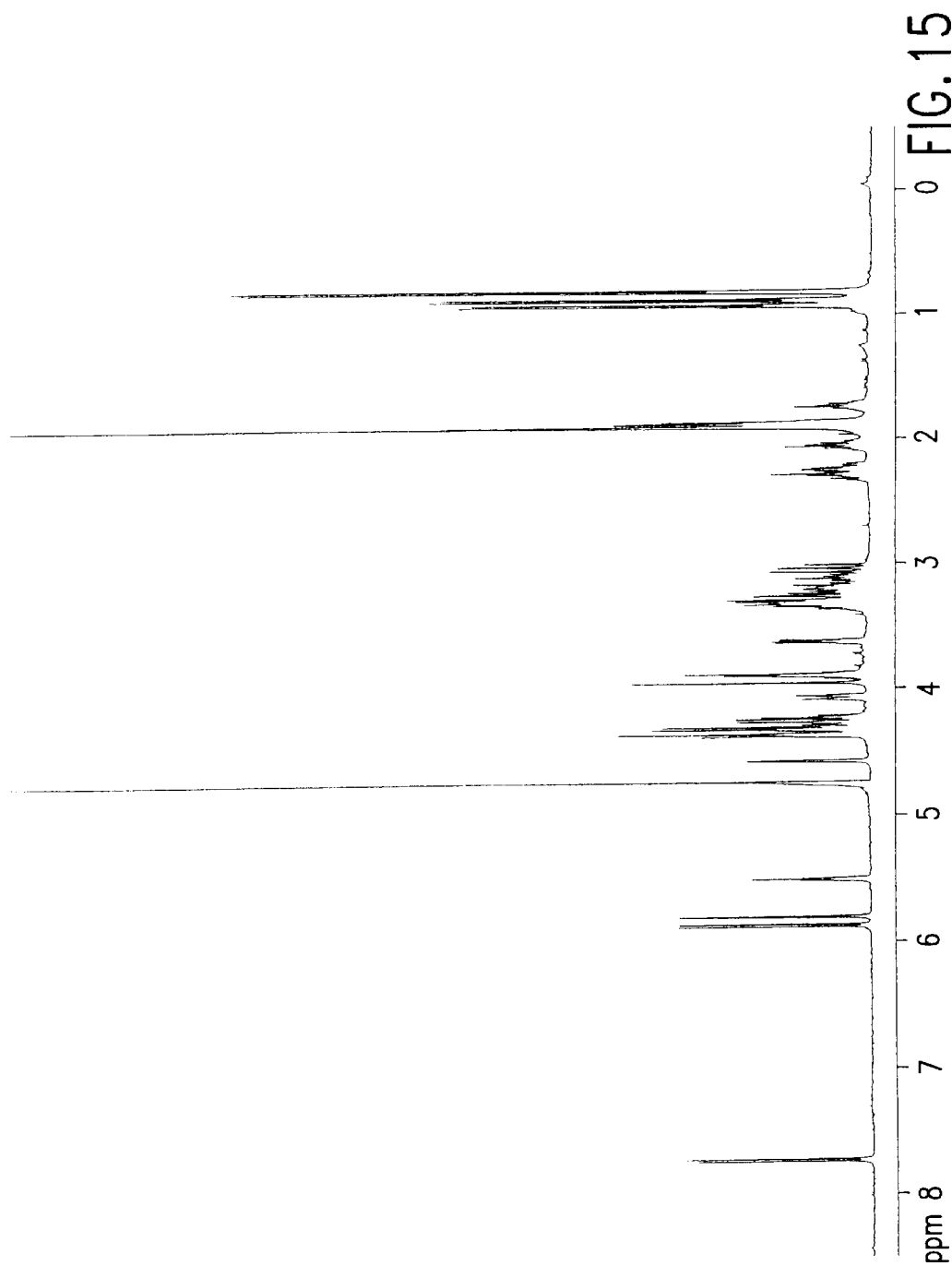
FIG. 15. Proton NMR spectrum of AA-896-C3 in $D_2O$ at 400 MHz

AA-896-C3
a) Apparent Molecular Formula: $C_{37}H_{61}N_{11}O_{16}$
b) Molecular Weight: Positive Ion Electrospray MS m/z= 916.4 $(M+H)^+$; 459.0 $(M+2H)^{2+}$; Negative Ion Electrospray MS m/z=914.2 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 15.

Figure 16:
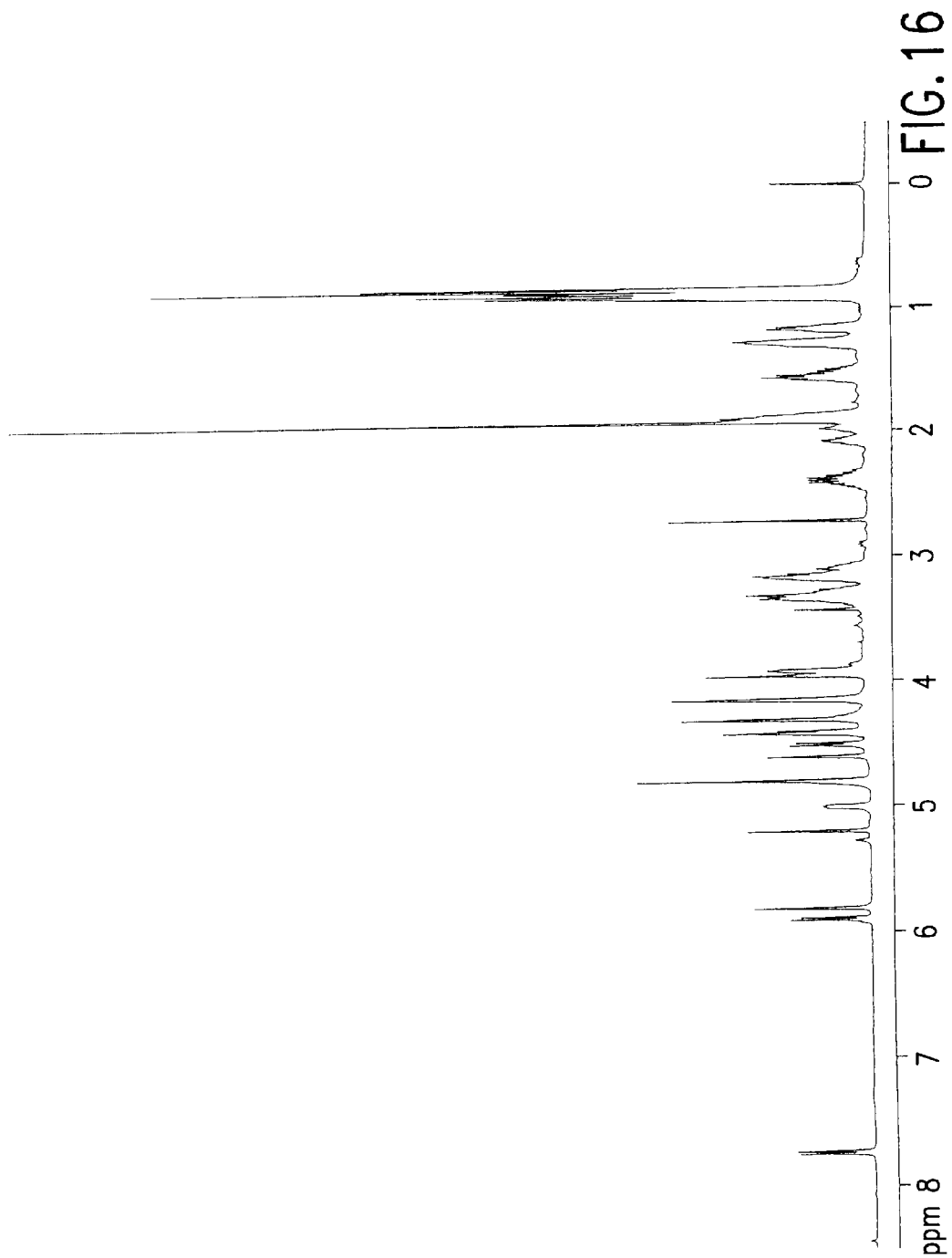
FIG. 16. Proton NMR spectrum of AA-896-B7 in $D_2O$ at 400 MHz

AA-896-B7 a) Apparent Molecular Formula: $C_{45}H_{75}N_{11}O_{18}$ b) Molecular Weight: Positive Ion Electrospray MS m/z= 1058.4 $(M+H)^+$; 529.7 $(M+2H)^{2+}$; Negative Ion Electrospray MS m/z=1056.6 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 16.

Figure 17:
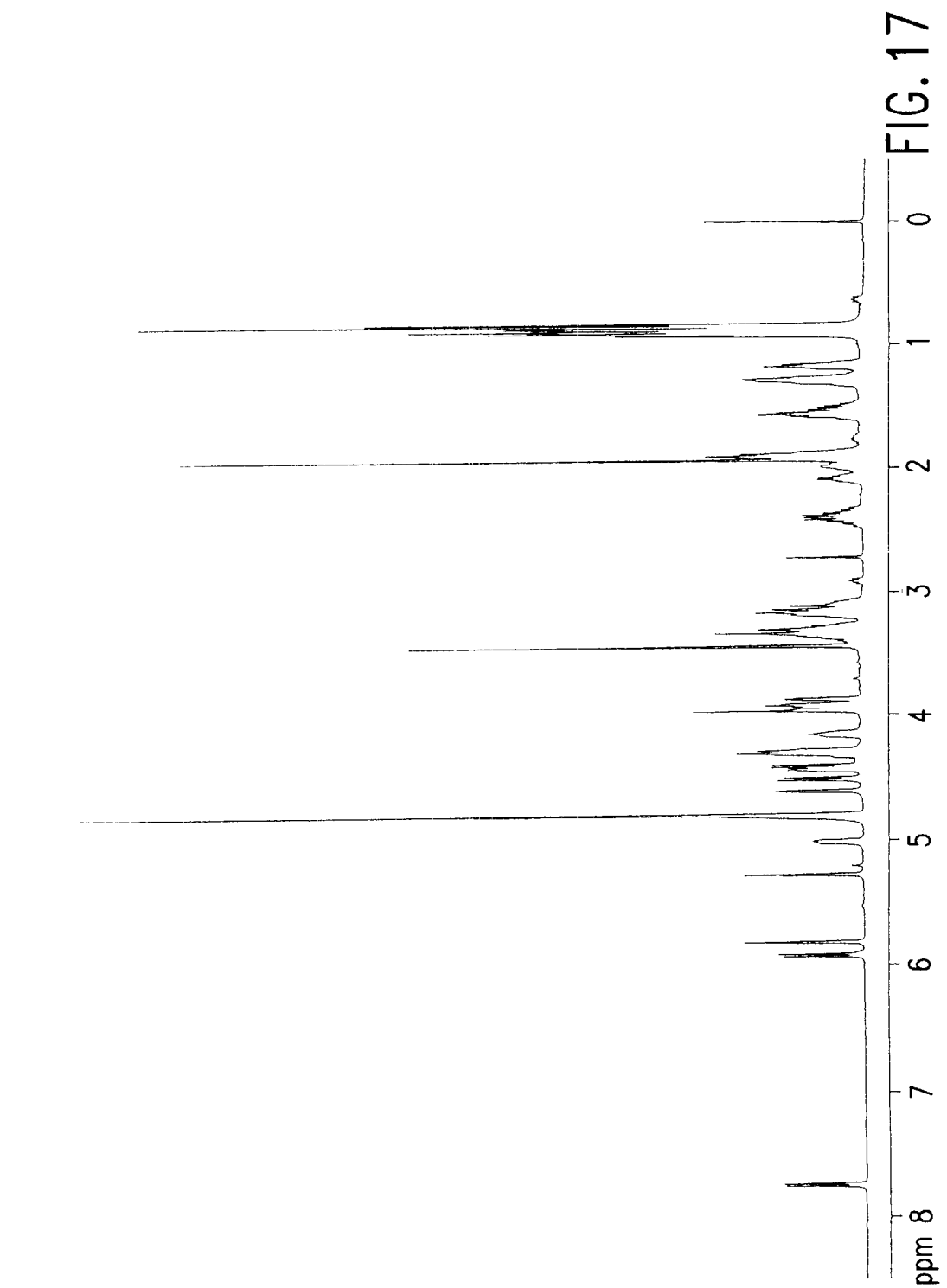
FIG. 17. Proton NMR spectrum of AA-896-B6 in $D_2O$ at 400 MHz

AA-896-B6 a) Apparent Molecular Formula: $C_{46}H_{77}N_{11}O_{18}$ b) Molecular Weight: Positive Ion Electrospray MS m/z= 1072.4 $(M+H)^+$; 536.6 $(M+2H)^{2+}$; Negative Ion Electrospray MS m/z=1070.5 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 17.

Figure 18:
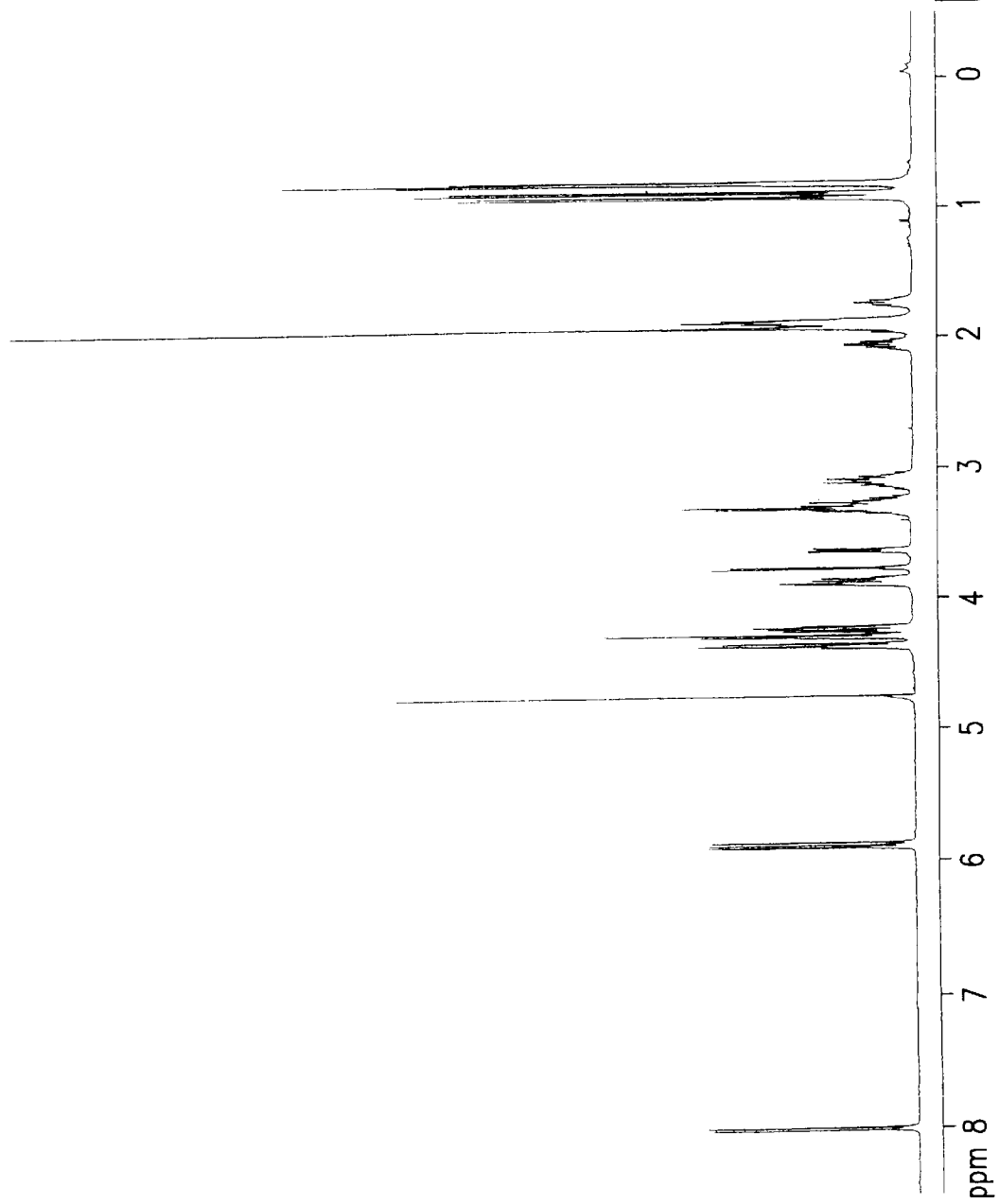
FIG. 18. Proton NMR spectrum of AA-896-C4 in $D_2O$ at 400 MHz

AA-896-C4 a) Apparent Molecular Formula: $C_{32}H_{52}N_{10}O_{14}$ b) Molecular Weight: Positive Ion Electrospray MS m/z= 801.4 $(M+H)^+$; 401.8 $(M+2H)^{2+}$; Negative Ion Electrospray MS m/z=799.2 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 18.

Figure 19:
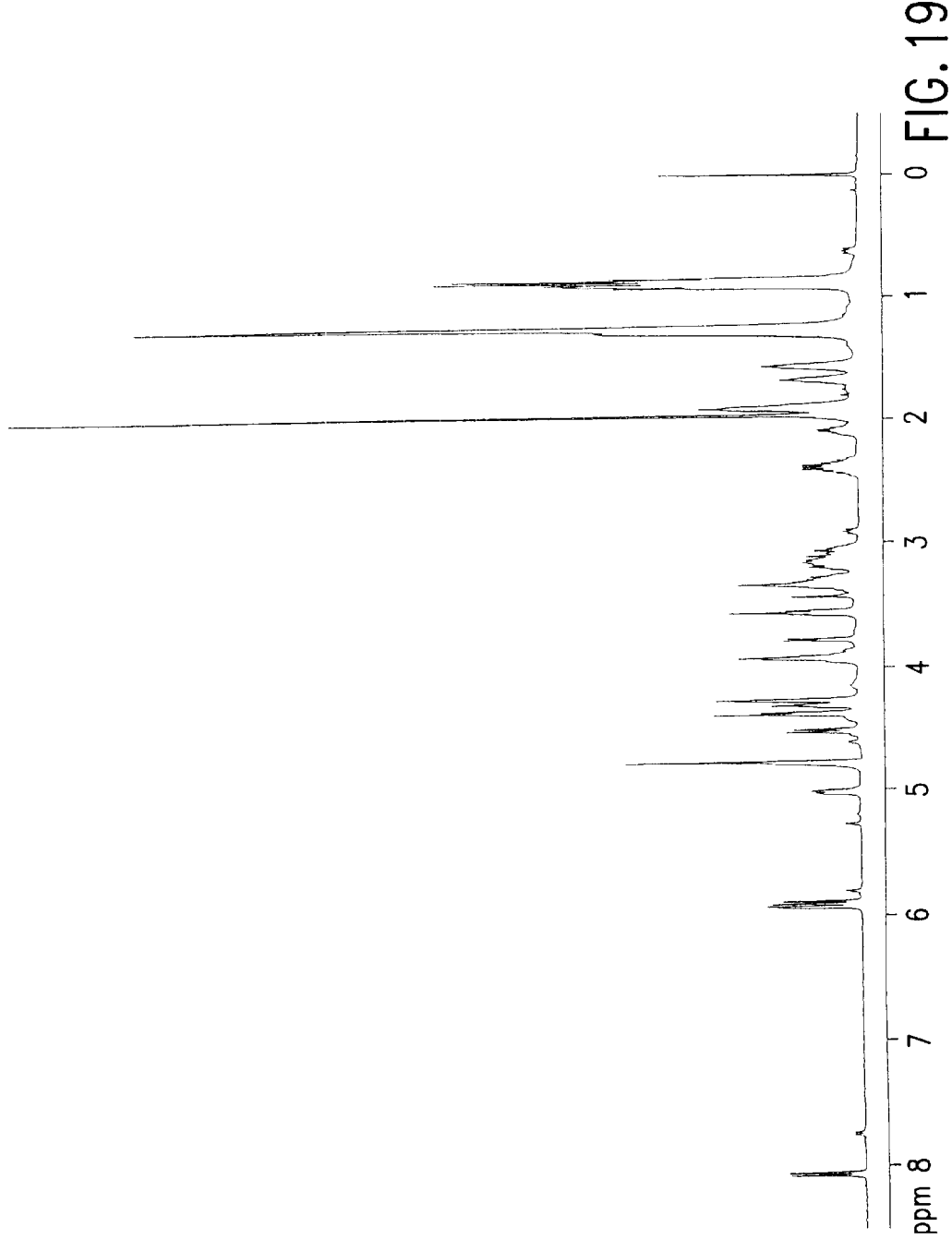
FIG. 19. Proton NMR spectrum of AA-896-A5 in $D_2O$ at 400 MHz

AA-896-A5 a) Apparent Molecular Formula: $C_{46}H_{79}N_{13}O_{16}$ b) Molecular Weight: Positive Ion Electrospray MS m/z= 1070.5 $(M+H)^+$; 535.8 $(M+2H)^{2+}$; Negative Ion Electrospray MS m/z=1068.7 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 19.

Figure 20:
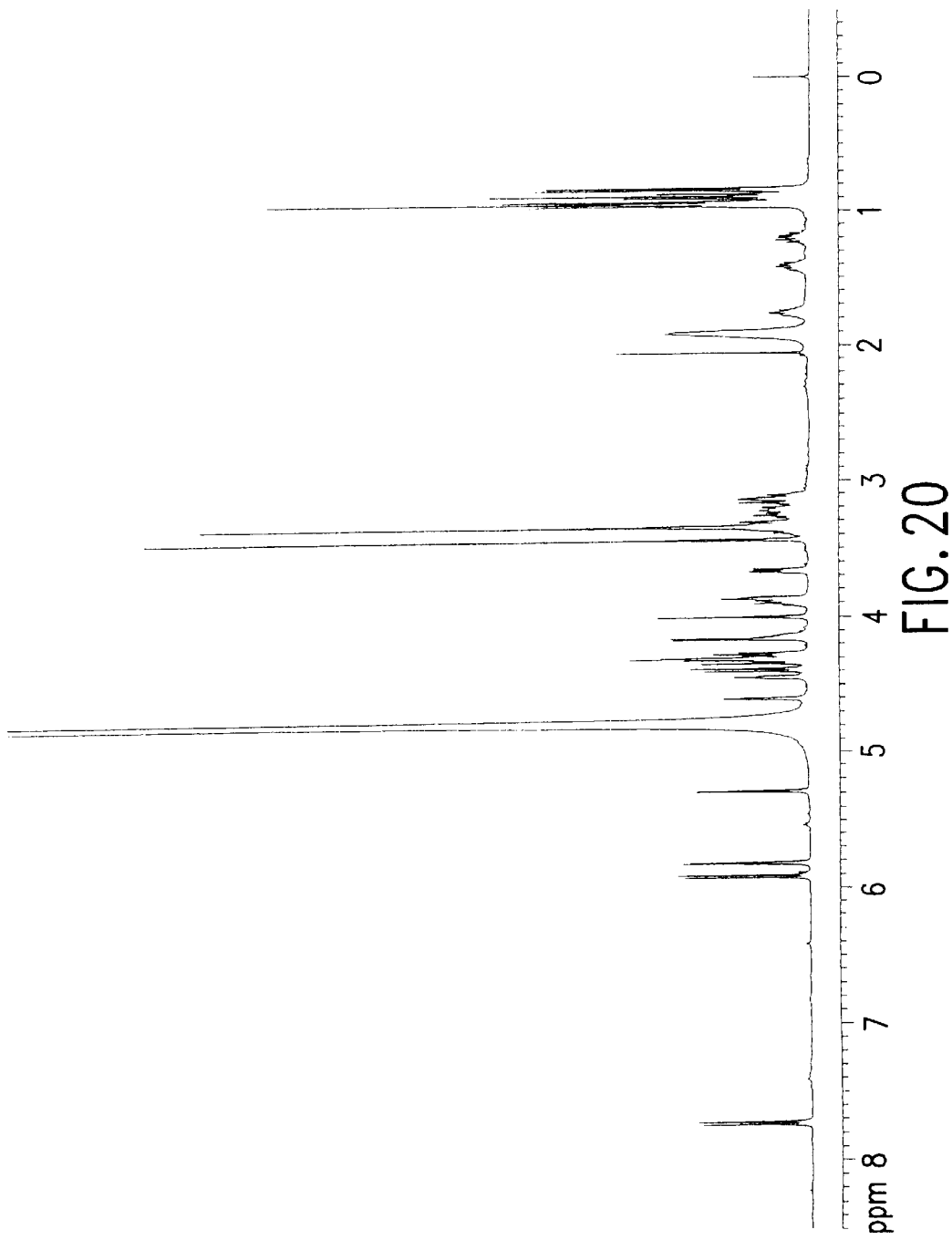
FIG. 20. Proton NMR spectrum of AA-896-C5 in $D_2O$ at 400 MHz

AA-896-C5 a) Apparent Molecular Formula: $C_{39}H_{65}N_{11}O_{17}$ b) Molecular Weight: Positive Ion Electrospray MS m/z= 960.4 $(M+H)^+$; 480.9 $(M+2H)^{2+}$; Negative Ion Electrospray MS m/z=958.3 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 20.

Figure 21:
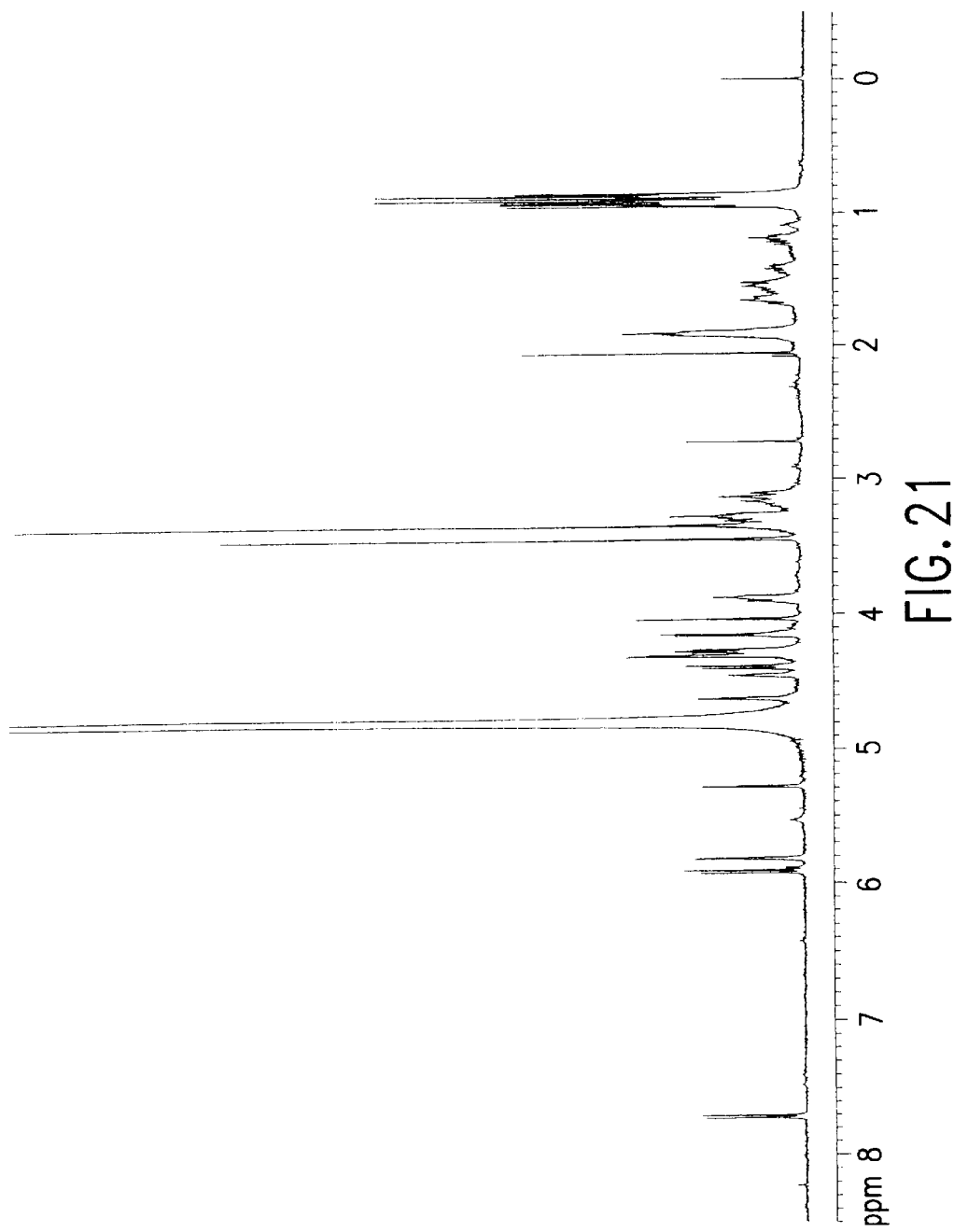
FIG. 21. Proton NMR spectrum of AA-896-D4 in $D_2O$ at 400 MHz

AA-896-D4 a) Apparent Molecular Formula: $C_{39}H_{65}N_{11}O_{16}$ b) Molecular Weight: Positive Ion Electrospray MS m/z= 944.4 $(M+H)^+$; 472.8 $(M+2H)^{2+}$; Negative Ion Electrospray MS m/z=942.4 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 21.

Figure 22:
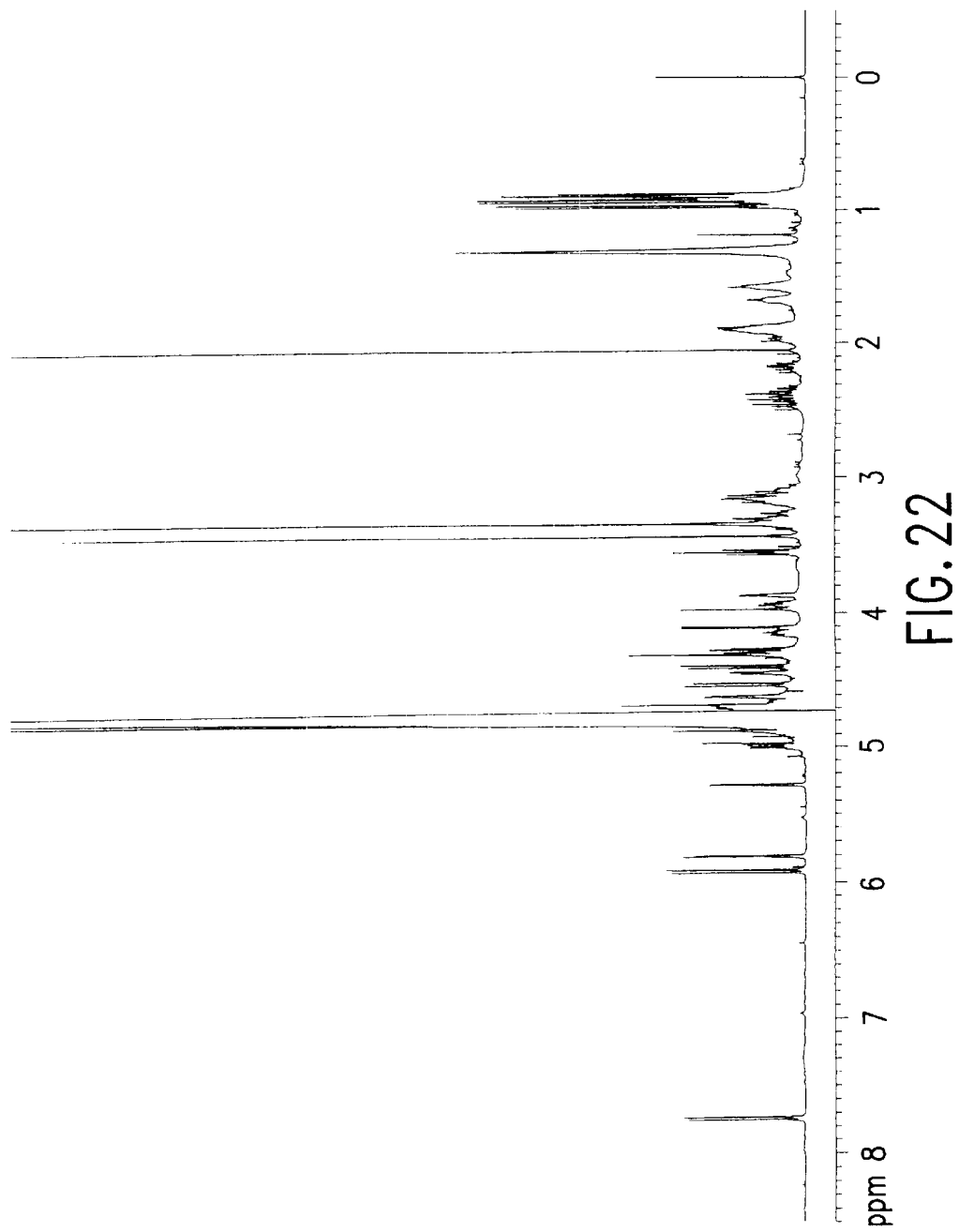
FIG. 22. Proton NMR spectrum of AA-896-A6 in $D_2O$ at 400 MHz

AA-896-A6 a) Apparent Molecular Formula: $C_{48}H_{82}N_{14}O_{19}$ b) Molecular Weight: Positive Ion Electrospray MS m/z= 1159.5 $(M+H)^+$; 580.5 $(M+2H)^{2+}$; Negative Ion Electrospray MS m/z=1157.5 $(M-H)^-$ c) Ultraviolet Absorption Spectrum: $\lambda_{max}$ nm (acetonitrile-water)=262 d) Proton Magnetic Resonance Spectrum: (400 MHz $D_2O$) See FIG. 22.

Strains

Certain AA-896 antibiotics of the invention are produced by fermentation of mutant derivative strains of Streptomyces spp. LL-AA896 (LL4774). These microorganisms are maintained in the culture collection of American Home Products, Wyeth-Ayerst Research, Pearl River, N.Y. as culture numbers LL4794, LL4802, LL4808, LL4889 and LL4892. A viable culture of these microorganisms is deposited under the Budapest Treaty with the Patent Culture Collection Laboratory, Northern Regional Research Center, U.S. Department of Agriculture, Peoria, Ill. 61604, and added to its permanent collection.

| Wyeth-Ayerst culture collection # | NRRL accession # |
|---|---|
| LL4774 | NRRL 30471 |
| LL4794 | NRRL 30472 |
| LL4802 | NRRL 30473 |
| LL4808 | NRRL 30474 |
| LL4889 | NRRL 30475 |
| LL4892 | NRRL 30476 |
| LL4879 | NRRL 30477 |

It is to be understood that the production of the antibiotics of the invention is not limited to the particular mutants defined above which are for illustrative purposes only. In fact, it is desired and intended to include the use of mutants as described herein and those produced by additional exposure of the above defined mutants to X-radiation, ultraviolet radiation, N'-methyl-N'-nitro-N-nitrosoguanidine, ethylmethane sulfonate and the like. Strains presented are all derivatives of LL-AA896. A culture stock designated LL4774 is derived from LL-AA896 and served as the starting point for the work described. Mutants accumulating LL-AA896 components, biosynthetic intermediates or compounds not detected in LL4774 are derived by NTG mutagenesis of LL4774 or various industrial derivatives of LL4774.

Mutagenesis

The described strains are obtained via N-methyl-N'-nitro-N-nitrosoguanidine (NTG) mutagenesis. Cells are grown in TSBG (Tryptic soy broth [Difco] supplemented with 20 g/L glucose) for approximately 24 hours and then are sonicated for 20–60" to disperse mycelial pellets to variably-sized mycelial fragments. The sonicated suspension is pelleted, re-suspended in fresh TSBG containing 100–1000 μg/ml NTG and dosed for 5–120 minutes at 30° C. with shaking. The dosed cells are then pelleted, re-suspended in fresh TSBG and grown overnight at 30° C. The overnight cells are then sonicated for 5–30" to disrupt mycelial pellets. The mutagenized cells are stored as a 20% glycerol stock at −70° C.

Culture Preservation

Strains are preserved as frozen whole cells (frozen vegetative mycelia, FVM) prepared from cells grown for 24 hours in TSBG (Tryptic soy broth [Difco] supplemented with 20 g/L glucose). Glycerol is added to 20% and the cells are frozen at −70° C.

Biological Activity

In Vitro Evaluation of AA-896 Compounds as Antibacterial Agents

The in vitro antibacterial activity of AA-896-A1, AA-896-A2, AA-896-A3, AA-896-A4, AA-896-A5, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-D1, AA-896-D2 and AA-896-D3 is determined against a spectrum of Gram-positive and Gram-negative bacteria by a standard broth dilution method. Serial dilution of the compounds are made in Mueller-Hinton broth and inoculated with a bacterial suspension. The lowest concentration of compound that inhibited the growth of a bacterial strain after 18 hours of incubation at 35° C. is reported as the minimal inhibitory concentration (MIC) for that strain. The results are given in the following table.

| Antimicrobial Activity (MIC, μg/mL) of AA-896 Compounds | | | | | | | |
|---|---|---|---|---|---|---|---|
| | AA-896-A1 | AA-896-B3 | AA-896-B4 | AA-896-A4 | AA-896-C2 | AA-896-C1 | AA-896-D2 |
| E. coli GC 4559 | 32 | >32 | 8 | 32 | >32 | >32 | 32 |
| E. coli GC 4560 | <=0.03 | 0.06 | <=0.06 | 0.12 | 2 | 1 | 0.25 |
| E. coli GC 3226 | 8 | 32 | 64 | 8 | 16 | 32 | 16 |
| S. marcescens GC 4077 | >32 | >32 | >64 | >32 | >32 | >32 | >32 |
| P. rettgeri GC 4530 | >32 | >32 | >64 | >32 | >32 | >32 | >32 |
| M. morganii GC 4531 | >32 | >32 | >64 | >32 | >32 | >32 | >32 |
| K. pneumoniae GC 4534 | >32 | >32 | 16 | >32 | >32 | >32 | >32 |
| E. cloacae GC 3783 | 0.5 | 16 | 8 | 1 | 16 | 32 | 16 |
| P. aeruginosa GC 4532 | 32 | >32 | 64 | 32 | 32 | >32 | 32 |
| S. aureus GC 4536 | 4 | >32 | 64 | 8 | >32 | >32 | >32 |
| S. aureus GC 1131 | 4 | >32 | 64 | 8 | >32 | >32 | >32 |
| CNS GC 4537 | 2 | >32 | 64 | 4 | >32 | >32 | >32 |
| CNS GC 4538 | 1 | >32 | 32 | 2 | >32 | >32 | >32 |
| CNS GC 4547 | 4 | >32 | >64 | 8 | >32 | >32 | >32 |
| E. faecalis GC 842 | 32 | >32 | >64 | 32 | >32 | >32 | >32 |
| E. faecalis GC 2242 | 32 | >32 | >64 | 32 | >32 | >32 | >32 |
| E. coli GC 2203 | 16 | >32 | 32 | 16 | 16 | 32 | 16 |
| P. aeruginosa GC 2214 | 16 | >32 | 32 | 32 | 32 | 32 | 32 |
| S. aureus GC 2216 | 8 | >32 | 64 | 4 | >32 | >32 | >32 |
| E. faecalis GC 4555 | 16 | >32 | 64 | 32 | >32 | >32 | >32 |

| | AA-896-D3 | AA-896-D1 | AA-896-C3 | AA-896-B7 | AA-896-B6 | AA-896-C4 | AA-896-C5 |
|---|---|---|---|---|---|---|---|
| E. coli GC 4559 | >32 | >32 | 32 | 64 | 32 | >32 | 4 |
| E. coli GC 4560 | 0.25 | 1 | 0.5 | <=0.06 | <=0.06 | 4 | <=0.06 |
| E. coli GC 3226 | 32 | 32 | 32 | >64 | 64 | >32 | 16 |
| S. marcescens GC 4077 | >32 | >32 | >32 | >64 | >64 | >32 | >64 |
| P. rettgeri GC 4530 | >32 | >32 | >32 | >64 | >64 | >32 | >64 |
| M. morganii GC 4531 | >32 | >32 | >32 | >64 | >64 | >32 | >64 |
| K. pneumoniae GC 4534 | >32 | >32 | >32 | 64 | 32 | >32 | 8 |
| E. cloacae GC 3783 | >32 | 32 | 8 | 16 | 8 | >32 | 1 |
| P. aeruginosa GC 4532 | >32 | 32 | 32 | >64 | >64 | 32 | 32 |
| S. aureus GC 4536 | >32 | >32 | >32 | >64 | >64 | >32 | 8 |
| S. aureus GC 1131 | >32 | >32 | >32 | >64 | >64 | >32 | 16 |
| CNS GC 4537 | >32 | >32 | >32 | >64 | >64 | >32 | 16 |
| CNS GC 4538 | >32 | >32 | >32 | >64 | 64 | >32 | 4 |
| CNS GC 4547 | >32 | >32 | >32 | >64 | >64 | >32 | 16 |
| E. faecalis GC 842 | >32 | >32 | >32 | >64 | >64 | >32 | >64 |
| E. faecalis GC 2242 | >32 | >32 | >32 | >64 | >64 | >32 | >64 |
| E. coli GC 2203 | 32 | >32 | 16 | >64 | 64 | >32 | 16 |
| P. aeruginosa GC 2214 | 32 | 32 | 16 | >64 | 64 | 32 | 32 |
| S. aureus GC 2216 | >32 | >32 | >32 | >64 | >64 | >32 | 16 |
| E. faecalis GC 4555 | >32 | >32 | >32 | >64 | >64 | >32 | 32 |

In Vivo Evaluation of AA-896-A1

The antibacterial efficacy of AA-896-A1 in vivo against acute lethal infection in mice is established by infecting mice with *Staphylococcus aureus* Smith or *Streptococcus pneumoniae*. The mice are treated with AA-896-A1. The results are given in Table 2.

TABLE 2

In vivo antimicrobial activity of AA-896-A1

| Organism | $ED_{50}$ range, mg/kg (95% confidence limit) |
| --- | --- |
| *Staphylococcus aureus* Smith | 0.83–1.46 |
| *Streptococcus pneumoniae* | 8.0–16.0 |

Compounds AA-896-A1, AA-896-A2, AA-896-A3, AA-896-A4, AA-896-A5, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-D1, AA-896-D2 and AA-896-D3 as well as other minor components derive their utility from their antibacterial activity. For example, these compounds may be used in the suppression of bacterial infections, as a topical antibacterial agent or as a general disinfectant.

Further, compounds of the invention may be obtained as pharmaceutically acceptable salts which are those derived from such organic and inorganic acids as: acetic, trifluoroacetic, lactic, citric, tartaric, formate, succinic, maleic, malonic, gluconic, hydrochloric, hydrobromic, phosphoric, nitric, sulfuric, methanesulfonic, and similarly known acceptable acids. Additionally, compounds of the invention may form calcium, potassium, magnesium, or sodium salts. The pharmaceutically acceptable salts of compounds of the invention are prepared using conventional procedures.

Compounds of the invention have centers of asymmetry. The compounds of the invention may, therefore, exist in at least two and often more stereoisomeric forms. The present invention encompasses all stereoisomers whether free from other stereoisomers or admixed with other stereoisomers in any proportion and thus includes, for instance, racemic mixtures of enantiomers as well as the diastereomeric mixtures of isomers. The absolute configuration of any substantially pure compound may be determined by any suitable method including conventional X-ray crystallography. It is understood that compounds of this invention, if crystalline, encompasses all crystalline forms.

In therapeutic use, the compounds of this invention may be administered in the form of conventional pharmaceutical composition appropriate for the intended use as antibacterials. Such compositions may be formulated so as to be suitable for oral, parenteral or topical administration. The active ingredient may be combined in admixture with non-toxic pharmaceutical carrier may take a variety of forms, depending on the form of preparation desired for administration, i.e. oral, parenteral, or topical.

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotics of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotics of the invention.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an antibacterially effective amount of a compound of this invention and a pharmaceutically acceptable carrier.

The present invention further provides a method of treating bacterial infections in warm-blooded animals including man, which comprises providing to the afflicted warm-blooded animals an antibacterially effective amount of a compound or a pharmaceutical composition of a compound of the invention. The invention will be more fully described in conjunction with the following specific examples which are not to be construed as limiting the scope of the invention.

Inoculum Development, Fermentation Media and Conditions

Cultivation of mutant strains of Streptomyces LL-AA896 designated above may be carried out in a wide variety of liquid culture media under aerobic conditions. Media which are useful for the production of LL-AA896 antibiotics include an assimilable source of carbon, such as dextrin, dextrose, sucrose, molasses, starch, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as zinc, cobalt, iron, boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as polypropylene glycol may be added as needed. In certain preferred embodiments of the invention, the media and conditions described below are employed.

Fermentations are inoculated from cells grown in TSBG medium at 30° C. for 24 hr with shaking on a gyro-rotary shaker. Shake-flask fermentations are performed at 26° C. for 5 days on a gyro-rotary shaker operating at 250 rpm (2" stroke). Ten-liter fermentations are performed at 26° C. for 5 days at 400–600 rpm with1 vvm airflow. Fermentation at 300 liters is similarly performed with agitation at 170–200 rpm for 5–9 days at 26° C. Antifoam, such as Macol P2000, is added to fermentor medium at 0.2%. Three hundred-liter fermentations employ a two-stage inoculum development with each successive cycle grown for 24 hours in TSBG at 30° C. The composition of the media employed in the examples is presented in the table below. The strains described may be fermented in any of the media listed below beyond the specific examples described Composition of Fermentation Media

| Component | BPM21 | BPM21P | BPM23A |
| --- | --- | --- | --- |
| Maltrin M180 (Grain Processing Corp) | 80.0 g/L | — | 80.0 g/L |
| Maltrin M500 (Grain Processing Corp) | — | 80.0 g/L | — |
| Glucose (Sigma) | 5.0 g/L | 5.0 g/L | 5.0 g/L |
| Nutrisoy soyflour (Archer Daniels Midland) | 35.0 g/L | 35.0 g/L | — |
| HY YEST 441 (Quest) | — | — | 20.0 g/L |
| $CaCO_3$ | 7.0 g/L | 7.0 g/L | 7.0 g/L |
| (Mississippi Lime) L-methionine (Sigma) | 2.0 g/L | 2.0 g/L | 1.5 g/L |
| L-leucine (Sigma) | — | — | 1.5 g/L |
| L-arginine (Sigma) | — | — | 1.5 g/L |

Analytical HPLC Analysis of AA-896 Antibiotics of the Invention

Fermentation broth is mixed with methanol (1/1) and cells/solids are then removed by centrifugation. The clarified, methanolic supernatant is applied to a wetted BAKERBOND™ SPE carboxylic acid extraction column (catalog # 7211-03). The column is then washed with 50% aqueous methanol and eluted with acetonitrile/water/ trifluoroacetic acid (70/30/0.5). The solvent is evaporated, and the residue is reconstituted in 0.4 mL methanol/water (1/1). Concentrates are analyzed using a Hewlett Packard model 1090 liquid chromatograph with photodiode array detection. The compounds are resolved by reverse phase chromatography using a YMC ODS-A 4.6×150 mm HPLC column, with a mobile phase of 10% acetonitrile: 0.01% trifluoroacetic acid (solvent A) and 50% acetonitrile: 0.01% trifluoroacetic acid (solvent B). A linear gradient from 0% B to 100% B in 22 min, with a flow rate of 1 ml/min, is used for elution. Metabolites of interest are identified by the appearance of HPLC peaks that possess characteristic UV absorption spectra and retention times.

Analytical LC/MS Analysis of AA-896 Antibiotics of the Invention

Samples (10 microliters) are analyzed using a model HP1100 Hewlett Packard liquid chromatograph with tandem photodiode array and mass spectral detection. Compounds are resolved on a YMC ODS-A 4.6×150 mm C18 HPLC column using linear gradient from 10 to 50% mobile phase B (0.05% trifluoroacetic acid in acetonitrile) in mobile phase A (0.05% trifluoroacetic acid in water) over 25 minutes. The flow rate is 0.8 ml/min. A total scan UV chromatogram is acquired over a scan range from 190 to 400 nanometers. UV spectra are acquired throughout the run from 190 to 400 nanometers with scan step of 2 nanometers. After emerging from the UV flow cell, the effluent stream is split 3:1 with a flow of 0.2 ml/min. going to a Finnigan LCQ ion trap mass spectrometer and the remainder going to waste. The mass spectrometer is fitted with an electrospray ionization (ESI) probe and is operated in alternating positive-ion and negative-ion full scan (100–2000 mass units) mode. The spray needle voltage is set to 6 kV for positive and 4.5 kV for negative. The capillary voltages are set at 29 and −10 for positive and negative, respectively. The capillary temperature is set to 200° C. Nitrogen is used as the sheath and auxiliary gasses which, are set to 60 and 25 units, respectively.

General Procedure for Purification of AA-896 Components

Antibiotics AA-896-A1, AA-896-A2, AA-896-A3, AA-896-A4, AA-896-A5, AA-896-A6, AA-896-B1, AA-896-B2, AA-896-B3, AA-896-B4, AA-896-B5, AA-896-B6, AA-896-B7, AA-896-C1, AA-896-C2, AA-896-C3, AA-896-C4, AA-896-C5, AA-896-D1, AA-896-D2, AA-896-D3 and AA-896-D4 as well as other minor components are purified form the cultured broth of various strains of Streptomyces spp. LL-AA896. The antibiotics are recovered from the clarified broth by adsorption onto HP20 resin followed by desorption from the resin using mixtures of organic solvents and water with small amounts of acid to control pH. The residues remaining after removal of the solvents are purified by ion exchange chromatography on a carboxylic acid resin to give a purified antibiotic complex. Individual antibiotics are then purified by HPLC on reversed-phase ODS support, typically using mobile phases comprised of acetonitrile-aqueous ammonium acetate buffer combinations or acetonitrile-water combinations with small amounts of trifluoroacetic acid. Methanol may be substituted for acetonitrile in some instances.

The invention is further described in conjunction with the following non-limiting examples. All components may be purified from the complex in a manner similar to the examples given.

The following examples illustrate the preparation of the compounds of the invention by fermentation procedures and as such are not to be considered as limiting the invention set forth in the claims appended hereto.

EXAMPLE 1

Strain LL4808 is fermented for 5 days in medium BPM21 shake-flasks. HPLC analysis of carboxylic acid column concentrates prepared from fermentation broth revealed the presence of an array of related components as judged by UV adsorption spectra and chromatographic elution. The major components observed display the following approximate retention times and relative retention times with respect to AA-896-A1:

| Observed retention times (min) | RRT with respect to AA-896-A1 |
| --- | --- |
| 5.65 | 0.42 |
| 7.15 | 0.53 |
| 13.52 | 1.00 |
| 15.54, 15.78 | 1.15, 1.17 |
| 16.64, 16.83 | 1.23, 1.24 |
| 17.97, 18.37 | 1.32, 1.36 |
| 19.09, 19.31 | 1.41, 1.43 |

Analysis by LC/MS allowed further characterization of the metabolites. The data obtained are summarized in the following table. All peaks showed UV spectrum with $\lambda max=262$ nm.

| LC/MS data for strain LL4808 producing the AA-896 complex. | | |
| --- | --- | --- |
| Compound | $(M + H)^+$ | Retention time (min.) |
| AA-896 B1 | 1114.5 | 22.9 |
| AA-896 B5 | 1072.5 | 20.0 |
| AA-896 B6 | 1072.5 | 19.2 |
| AA-896 B2 | 1100.5 | 22.1 |
| AA-896 A2 | 1187.4 | 14.8 |
| AA-896 A1 | 1215.4 | 16.7 |
| AA-896 B3 | 1086.5 | 20.1 |
| AA-896 B4 | 1086.5 | 20.4 |
| AA-896 A4 | 1201.5 | 16.6 |
| AA-896 C2 | 932.4 | 7.4 |
| AA-896 C1 | 946.4 | 7.5 |
| AA-896 D2 | 916.4 | 9.1 |
| AA-896 D1 | 930.4 | 9.3 |
| AA-896 A3 | 1199.4 | 16.8 |
| AA-896 C3 | 916.3 | 7.5 |
| AA-896 B7 | 1058.4 | 18.7 |
| AA-896 C5 | 960.4 | 9.8 |
| AA-896 D4 | 944.4 | 11.3 |
| AA-896 A5 | 1159.5 | 13.1 |

Further analysis by LC/MS allows detection of additional AA-896 metabolites produced by strain LL4808. The data obtained are summarized in the following table. All peaks showed UV spectrum with $\lambda max=262$ nm.

| $(M + H)^+$ | Retention time (min.) |
| --- | --- |
| 930.4 | 8.4 |
| 930.3 | 9.7 |
| 944.4 | 11.0 |
| 948.3 | 8.0 |
| 960.4 | 9.3 |
| 1042.4 | 18.8 |
| 1042.4 | 19.1 |
| 1056.5 | 20.1 |
| 1056.5 | 20.3 |
| 1058.4 | 17.2 |
| 1058.5 | 17.4 |
| 1058.4 | 17.7 |
| 1058.4 | 19.0 |
| 1072.5 | 18.9 |
| 1084.5 | 22.8 |
| 1084.5 | 23.0 |
| 1086.6 | 20.6 |
| 1086.5 | 21.5 |
| 1086.5 | 21.9 |
| 1100.5 | 21.7 |
| 1100.5 | 22.7 |
| 1114.5 | 23.1 |
| 1128.5 | 24.0 |
| 1128.5 | 24.1 |
| 1125.5 | 24.5 |
| 1128.5 | 24.7 |
| 1142.5 | 26.1 |
| 1142.5 | 26.3 |
| 1156.4 | 23.3 |
| 1156.5 | 23.6 |
| 1156.5 | 23.9 |
| 1170.5 | 24.1 |
| 1170.5 | 24.3 |
| 1170.5 | 24.6 |
| 1170.5 | 24.8 |
| 1188.5 | 25.9 |

EXAMPLE 2

LL4794 is fermented in medium BPM21 P at the 300-liter scale. HPLC analysis of concentrates prepared from fermentation broth revealed a component profile equivalent to that seen in the BPM21 shake-flask fermentation described in example 1.

To afford isolation of the complex one hundred thirty liters of methanol is added to 286 liter of the LL4794 fermentation broth. Twelve kilograms of celite filter aid are added and mixture stirred before filtration. Sixty liters water is added to the filtrate which is then loaded at 2 liters per minute onto a column packed with washed HP20 resin suspended in water making a bed volume of 30 liters. The column is washed with 120 liters water then eluted with 360 liters methanol-water-concentrated hydrochloric acid (80:19.8:0.2) while collecting 20-liter fractions. After analyzing the fractions by HPLC for antibiotic content, the solvent is evaporated from the appropriate fractions (2 and 3) giving concentrates containing the crude antibiotic complex.

A portion of the concentrate (1.0L) from fraction 3 (total volume 1.7L) is chromatographed on Amberlite IRC-50 carboxylic acid cation exchange resin as follows: The hydrogen form IRC-50 resin is placed in a column forming a bed with dimensions 2.5 cm I.D.×49 cm L. The solution is loaded at 2 mL/min onto the column. This is followed by washes of the column first by 2 liters of water then with 2 liters of methanol-water (90:10) at a flow rate of 11 mL/min. The column is then eluted at 2 mL/min with a solution comprised of methanol-water-concentrated hydrochloric acid in the proportion 90:9.5:0.5 yielding after evaporation of the solvent 18.8 grams of purified antibiotic complex.

EXAMPLE 3

A solution of 1.47 grams of a purified antibiotic complex in 5 mL 25% acetonitrile-water containing 0.1% trifluoroacetic acid is chromatographed on a 50×250 mm Phenomenex Primesphere ODS preparative HPLC column previously equilibrated with mobile phase comprised of 25% B (acetonitrile containing 0.1% trifluoroacetic acid) in A (water containing 0.1% trifluoroacetic acid). Elution is carried out at 30 mL/min with a mobile phase gradient from 25% to 40% B in A over 120 minutes. Ultraviolet absorbance is monitored at 254 nanometers while fractions are collected at 1 minute intervals. Fractions are combined based on UV chromatogram, concentrated in vacuo and freeze-dried from water to yield fractions shown in the table below.

prised of 0.1M ammonium acetate pH 7.0 buffer. Elution is carried out at 10 mL/min with a mobile phase gradient from 0% to 40% acetonitrile in 0.1 M ammonium acetate pH 7.0 buffer over 60 minutes. Ultraviolet absorbance is monitored at 254 nanometers while fractions are collected at 1 minute intervals. AA-896-A1 (28.9 mg) is contained in the fraction eluting from 53 to 54 minutes. The fraction eluting from 52 to 53 minutes is concentrated in vacuo and freeze-dried from water to yield 23.2 mg of AA-896-A3.

A solution of 182.0 mg of Fraction 3 in 3 mL acetonitrile-0.1 M ammonium acetate pH 7.0 buffer (25:75) is chromatographed in three equal portions on a 50×250 mm Phenomenex Prodigy ODS preparative HPLC column previously equilibrated with mobile phase comprised of 25% acetonitrile in 0.1 M ammonium acetate pH 7.0 buffer. Elution is carried out at 20 mL/min with a mobile phase gradient from 25% to 35% acetonitrile in 0.1 M ammonium acetate pH 7.0 buffer over 120 minutes. Ultraviolet absorbance is monitored at 262 nanometers while fractions are collected at 1 minute intervals. The fraction eluting from 70 to 71 minutes is concentrated in vacuo and freeze-dried from water to yield 1.3 mg of AA-896-A5. The fractions eluting from 76 to 78 minutes are combined, concentrated in vacuo and freeze-dried from water to yield 4.3 mg of AA-896-B7. The fraction eluting from 99 to 100 minutes is concentrated in vacuo and freeze-dried from water to yield 1.9 mg of AA-896-B5.

The production and purification of AA-896-C1 is carried out as follows: To a solution of crude AA-896 complex (10.6 g in 500 ml water) 500 ml 0.5 sodium hydroxide is added dropwise while stirring. After 3 hours at 25° C., the solution is neutralized with 6N hydrochloric acid and is diluted to 1200 ml. The solution is passed through a column (2.5×30

| Fractions Derived from Preparative HPLC of an Antibiotic Complex | | | |
|---|---|---|---|
| Fraction | Retention Time (min) | Compound | Yield (mg) |
| 1 | 43–59 | AA-896-A1, AA-896-A3 and other minor components | 267.0 |
| 2 | 59–73 | Mixture of minor components | 141.2 |
| 3 | 73–95 | AA-896-B5, AA-896-B7, AA-896-B6, AA-896-A5 and other minor components | 184.9 |
| 4 | 96–109 | Mixture of minor components | 91.4 |
| 5 | 109–124 | Mixture of minor components | 31.8 |

A solution of 267.0 mg of Fraction 1 in 6 mL acetonitrile-0.1 M ammonium acetate pH 7.0 buffer (25:75) is chromatographed in three equal portions on a 21.2×250 mm Phenomenex Prodigy ODS preparative HPLC column previously equilibrated with mobile phase comprised of 25% acetonitrile in 0.1 M ammonium acetate pH 7.0 buffer. Elution is carried out at 10 mL/min with a mobile phase gradient from 25% to 45% acetonitrile in 0.1 M ammonium acetate pH 7.0 buffer over 60 minutes. Ultraviolet absorbance Is monitored at 254 nanometers while fractions are collected at 1 minute intervals. Fractions eluting from 31 to 34 minutes are combined, concentrated in vacuo and freeze-dried from water to yield 91.8 mg of AA-896-A1.

The fraction eluting from 30 to 31 minutes, containing a mixture of AA-896-A1 and AA-896-A3, is concentrated in vacuo and freeze-dried from water to yield a residue (57.8 mg). A solution of 54 mg of this residue in 2.5 mL 0.1 M ammonium acetate pH 7.0 buffer is chromatographed on a 21.2×250 mm Phenomenex Prodigy ODS preparative HPLC column previously equilibrated with mobile phase comcm) packed with BIO-RAD AGMP-50 resin (previously conditioned by washing with methanol followed by 0.5N hydrochloric acid and water). The resin is washed first with 1.5L water then with 1.0L methanol-water (1:1) and finally the complex is eluted with 2.2L of a mixture of methanol-water-ammonium hydroxide (50:46:4). The eluant is concentrated to aqueous and lyophilized to yield 3.5 grams of a residue enriched in AA-896-C1. Approximately 2.2 g of the residue (in 19 ml of starting mobile phase) is chromatographed on a 41.4×250 mm Microsorb C18 column. Following isocratic elution at 5 ml/min for 5 minutes with a mobile phase comprised of 5% solvent B (acetonitrile) in solvent A (0.1M aqueous ammonium acetate pH 7.0 buffer), gradient elution from 5% to 9% solvent B in solvent A over 60 minutes is carried out at 20 ml/min. This is followed by steep gradient elution at 20 ml/min to 100% B over an additional 10 minutes. Fractions comprised of eluant from 65 to 69 minutes are combined, concentrated and lyophilized to yield a residue weighing 69.6 mg. The residue is dissolved in 2.6 ml DMSO-water (1:1.3) and chromatographed on a 21.2×250 mm Prodigy ODS column using a mobile phase comprised of 20% methanol in 0.1 M aqueous ammonium acetate pH 7 buffer flowing at a rate of 10.0 ml/min to yield 32.2 mg AA-896-C1.

EXAMPLE 4

Strain LL4802 is fermented in medium BPM23A at the ten-liter scale for 5 days at 26° C. HPLC analysis of carboxylic acid concentrates prepared from fermentation broth revealed the presence of an array of related components as judged by UV adsorption spectra and chromatographic elution, with AA-896-A1 as the predominant metabolite The major components observed display the following approximate retention times and relative retention times with respect to AA-896-A1:

| Observed retention times (min) | RRT with respect to AA-896-A1 |
|---|---|
| 4.37 | 0.35 |
| 5.81 | 0.46 |
| 12.57 | 1.00 |
| 15.03, 15.22 | 1.20, 1.21 |
| 16.22, 16.39 | 1.29, 1.30 |
| 17.71, 18.01 | 1.41, 1.43 |
| 18.91, 19.10 | 1.50, 1.52 |

EXAMPLE 5

Strain LL4879 is fermented in multiple shake-flasks of medium BPM21. After 5 days incubation at 26° C. the flasks are pooled to yield approximately 1.5 liters of broth. A carboxylic acid column concentrate is then prepared from a sample of the pooled broth. HPLC analysis of the concentrate reveals the presence of a major component with characteristic UV absorption spectra, displaying an approximate retention time of 5.36 min, as well as associated minor components with approximate retention times of 6.33, 6.55 and 7.09 min. The calculated relative retention times with respect to component AA-896-A1 for the observed compounds are 0.40, 0.47, 0.48 and 0.52.

Analysis by LC/MS allows further characterization of the metabolites as shown in the table below. All chromatographic peaks showed UV spectrum with λmax=262 nm.

| Strain | Compound | 946.4 (M + H)$^+$ | Retention time (min.) |
|---|---|---|---|
| LL4879 | AA-896 C1 | 946.4 | 8.0 |
| LL4879 | AA-896 C5 | 960.3 | 9.9 |

To afford isolation of AA-896-C1, 6 ml of whole broth from strain LL4879 is centrifuged, the supernatant is collected and allowed to flow slowly through a bed of BAKERBOND carboxylic acid support packed in a 60 ml sintered glass funnel column (bed volume=20 cc; Prior to applying the compound, the support is washed with 60 ml of each of the following: methanol, 0.5% aqueous trifluoroacetic acid, and water). The column is washed with 60 ml methanol-water (50:50) and eluted with 60 ml of methanol-water (70:30 with 0.5% trifluoroacetic acid). The eluant is concentrated to aqueous and freeze-dried to give a solid (79.0 mg). The solid is chromatographed on a YMC ODS-A 250×20 mm column with a gradient mobile phase from 5 to 30% B (0.05% trifluoroacetic acid in acetonitrile) in A (0.05% trifluoroacetic acid in water) over 60 minutes at a flow rate of 4.0 ml/minute. Ultraviolet absorbance is monitored at 260 nm while 4 ml fractions are collected at 1 minute intervals. Fractions 51 and 52, which elute between 50 and 52 minutes, are combined, evaporated to a residue and freeze-dried from water to yield 0.9 mg of AA-896C1.

Alternatively, large-scale purification is carried out by centrifuging 1.5 liters of whole broth from mutant LL4879 and extracting the resulting cell pellet with 1 liter methanol. The solvent is removed in vacuo to give an aqueous solution which is combined with the supernatant and pumped slowly onto a bed of HP20 support packed in a 2.5×30 cm glass column (bed volume=75 cc). The column is washed with 1 liter water and eluted with 1 liter methanol-water (40:60). The eluant is concentrated to aqueous and freeze-dried to give a solid (2.35 g). The solid is chromatographed on a Prodigy 250×50 mm ODS column with a gradient mobile phase from 10 to 20% solvent B (0.05% trifluoroacetic acid in acetonitrile) in solvent A (0.05% trifluoroacetic acid in water) over 120 minutes at a flow rate of 10.0 ml/minute. Ultraviolet absorbance is monitored at 262 nm while 10 ml fractions are collected at 1 minute intervals. Fractions 72 to 75, which elute between 71 and 75 minutes, are combined, evaporated to a residue and freeze-dried from water to yield 96.6 mg of AA-896-C1.

The preparative HPLC column is further eluted with 600 ml 100% solvent B (0.05% trifluoroacetic acid in acetonitrile) which is collected as a single fraction and concentrated to a residue (1.66 grams). The residue is chromatographed on a Prodigy 250×50 mm ODS column with an isocratic mobile phase comprised of 15% solvent B (0.05% trifluoroacetic acid in acetonitrile) in solvent A (0.05% trifluoroacetic acid in water) using a flow rate gradient from 5 ml/min to 20 ml/min in 5 minutes. After 5 minutes, gradient elution commences from 15% to 30% B in A over 125 minutes at a flow rate of 20.0 ml/minute. Ultraviolet absorbance is monitored at 262 nm while 20 ml fractions are collected at 1 minute intervals. Fractions 54 to 62, which elute between 53 and 62 minutes, are combined and evaporated to a residue (151 mg). The residue is chromatographed on YMC 250×20 mm ODS-A column with an isocratic mobile phase comprised of 15% B (0.05% trifluoroacetic acid in acetonitrile) in A (0.05% trifluoroacetic acid in water) at a flow rate of 8.0 ml/minute. Ultraviolet absorbance is monitored at 262 nm while 8 ml fractions are collected at 1 minute intervals. Fraction 21, which elutes between 20 and 21 minutes, is evaporated to a residue and freeze-dried from water to yield 6.7 mg of AA-896C5.

EXAMPLE 6

Strain LL4889 is fermented in multiple shake-flasks of medium BPM21. After 5 days incubation at 26° C. the flasks are pooled to yield approximately 1.8 liters of broth. A carboxylic acid column concentrate is then prepared from a sample of the pooled broth. HPLC analysis of the concentrate reveals the presence of a major component with characteristic UV absorption spectra, displaying an approximate retention time of 6.47 min, as well as associated minor components with approximate retention times of 7.40, 8.11, 8.28 and 8.51 min. The calculated relative retention times with respect to component AA-896-A1 for the observed compounds are 0.48, 0.55, 0.60, 0.61 and 0.63.

Analysis by LC/MS allows further characterization of the metabolites as shown in the table below. All chromatographic peaks showed UV spectrum with λ max=262 nm.

| Strain | Compound | (M + H)⁺ | Retention time (min.) |
|---|---|---|---|
| LL4889 | AA-896 D1 | 930.4 | 9.6 |
| LL4889 | AA-896 D4 | 944.3 | 11.4 |

To afford isolation of the compounds of the example, 1.8 liters of LL4889 whole broth is centrifuged. The resulting cell pellet is extracted with 1 liter of methanol. The solvent is removed in vacuo to give an aqueous solution which is combined with the supernatant and pumped slowly onto a bed of HP20 support packed in a 2.5×30 cm glass column (bed volume=75 cc). The column is washed with 1 liter water then eluted with 1 liter methanol-water (40:60). The eluant is concentrated to aqueous and freeze-dried to give a solid (2.55 g). Approximately 493 mg of this solid is chromatographed on a YMC 250×20 mm ODS-A column with a gradient mobile phase from 20% to 40% solvent B (0.05% trifluoroacetic acid in acetonitrile) in solvent A (0.05% trifluoroacetic acid in water) over 60 minutes at a flow rate of 4.0 ml/minute. Ultraviolet absorbance is monitored at 262 nm while 4 ml fractions are collected at 1 minute intervals. Fractions 21 to 23, eluting between 20 and 23 minutes, contains AA-896D1. Fraction 27, which elutes between 26 and 27 minutes, is evaporated to a residue and freeze-dried from water to yield 5.7 mg of AA-896D4.

EXAMPLE 7

Strain LL4892 is fermented in multiple shake-flasks of medium BPM21. After 5 days incubation at 26° C. the flasks are pooled to yield approximately 1.8 liters of broth. A carboxylic acid column concentrate is then prepared from a sample of the pooled broth. HPLC analysis of the concentrate reveals the presence of an array of related components equivalent to that presented in example 1. Additionally, a novel component displaying an approximate retention time of 9.73 min (RRT 0.72) is also noted. The major metabolites observed are summarized in the following table:

| Observed retention times (min) | RRT with respect to AA-896-A1 |
|---|---|
| 5.61, 5.99 | 0.41, 0.44 |
| 7.08 | 0.52 |
| 9.73 | 0.72 |
| 11.60 | 0.80 |
| 13.53 | 1.00 |
| 15.58, 15.83 | 1.15, 1.17 |
| 16.71, 16.89 | 1.24, 1.25 |
| 18.14 | 1.34 |
| 19.24 | 1.42 |

Analysis by LC/MS allows further characterization of the metabolites as shown in the table below. All chromatographic peaks showed UV spectrum with λ max=262 nm.

| Strain | Compound | (M + H)⁺ | Retention time (min.) |
|---|---|---|---|
| LL4892 | AA-896 A6 | 1159.4 | 13.0 |
| LL4892 | AA-896 A2 | 1187.4 | 15.0 |

To afford isolation of compounds of the example, 1.8 L of whole broth from LL4892 is centrifuged and the resulting supernatant and cell pellet are collected. The pellet is then extracted with 1 liter of methanol. The solvent is removed in vacuo to give an aqueous solution which is combined with the supernatant and pumped slowly onto a bed of HP20 support packed in a 2.5×30 cm glass column (bed volume= 75 cc).

The column is washed with 1 liter water then with 1 liter methanol-water (40:60) and finally eluted with 1 liter 0.1% trifluoroacetic acid in methanol. The eluant is concentrated to a solid (2.10 g) which is dissolved in 100 ml water and applied slowly to 175 cc Varian Bondisil C18 support in a 350 ml Buchner funnel fritted-disk glass column. Using a water aspirator vacuum to pull solvent through the column, one liter each of the following are passed through the column: water, methanol-water (50:50), 100% methanol and 0.1% trifluoroacetic acid in methanol. The 100% methanol and 0.1% trifluoroacetic acid in methanol eluants are combined and diluted with water to four liters. This solution is slowly applied to a 2.5×30 cm column packed with 175 cc BAKERBOND carboxylic acid support (washed with 1 liter each of the following: methanol, 0.5% trifluoroacetic acid in water and water). After washing the column with 2 liters water and 2 liters methanol-water (50:50), elution is carried out with 1 liter 0.5% trifluoroacetic acid in methanol-water (70:30). The eluant is evaporated to a residue (263.2 mg) which is chromatographed on a YMC 250×20 mm ODS-A column with a gradient mobile phase from 20% to 40% solvent B (0.05% trifluoroacetic acid in acetonitrile) in solvent A (0.05% trifluoroacetic acid in water) over 90 minutes at a flow rate of 4.0 ml/min. Ultraviolet absorbance is monitored at 262 nm while 4 ml fractions are collected at 1 minute intervals. Fractions 50 to 53, eluting between 49 and 53 minutes, contains AA-896A2. Fractions 37 to 39, which elutes between 36 and 39 minutes, are evaporated to a residue and freeze-dried from water to yield 5.2 mg of AA-896 A6.

What is claimed is:

1. The compound AA-896-B1 which has the structure:

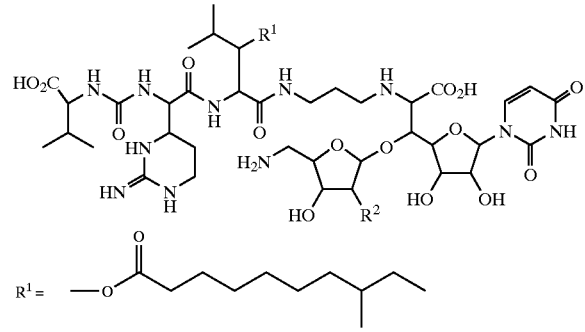

R¹ = and

R² = —OCH₃ or pharmaceutically acceptable salts thereof.

2. The compound AA-896-B5 which has the structure:
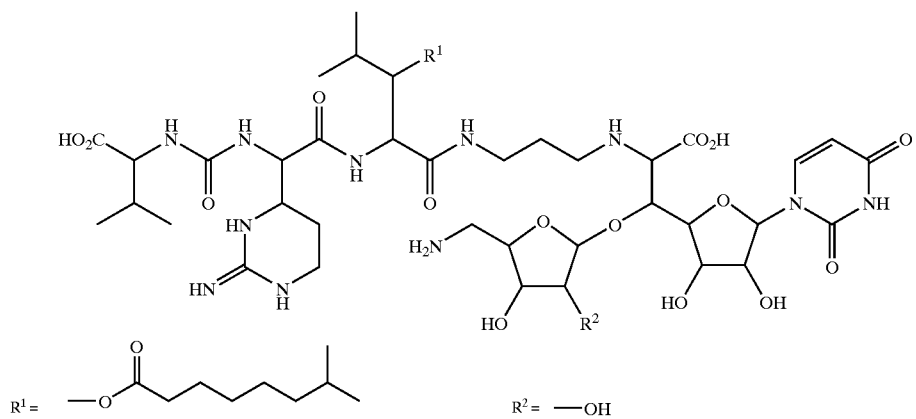
or pharmaceutically acceptable salts thereof.
3. The compound AA-896-B2 which has the structure:
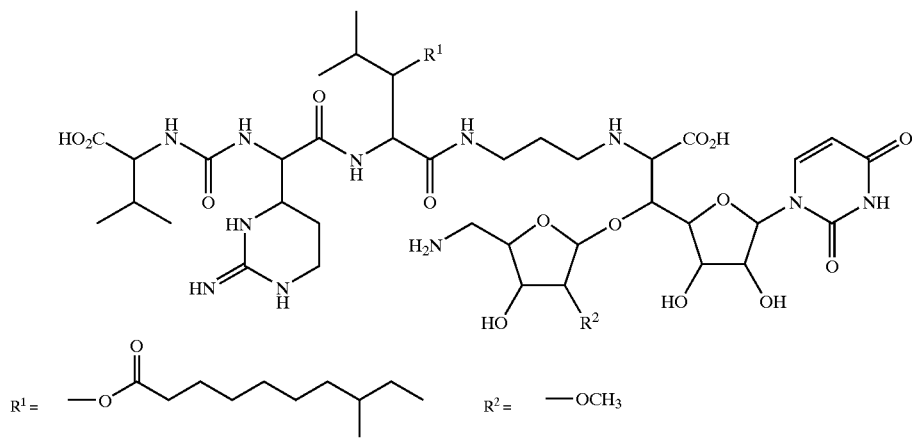
or pharmaceutically acceptable salts thereof.
4. The compound AA-896-A2 which has the structure:
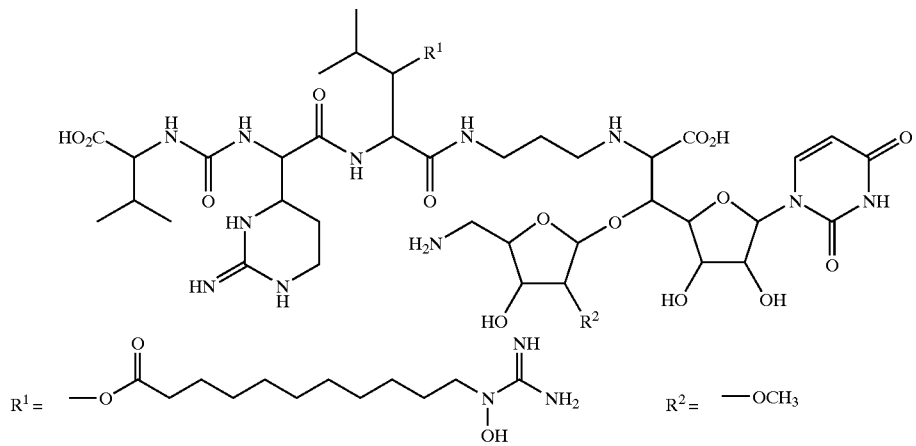
or pharmaceutically acceptable salts thereof.

5. The compound AA-896-A1 which has the structure:
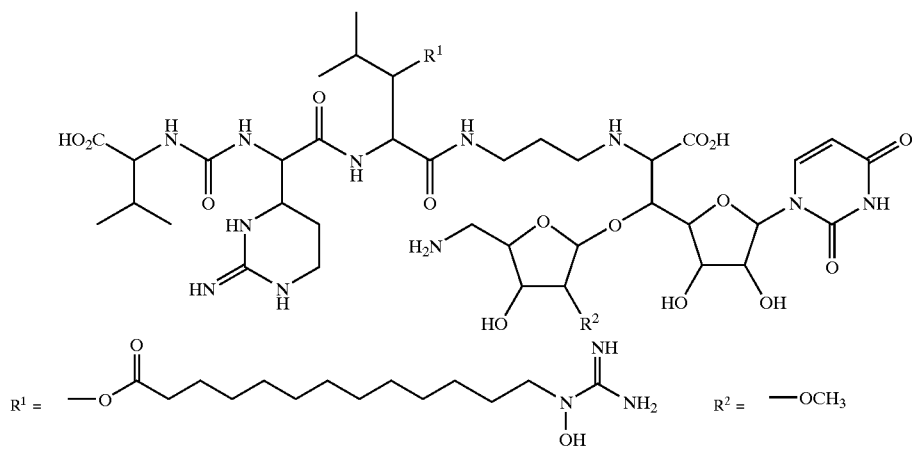
or pharmaceutically acceptable salts thereof.
6. The compound AA-896-B3 which has the structure:
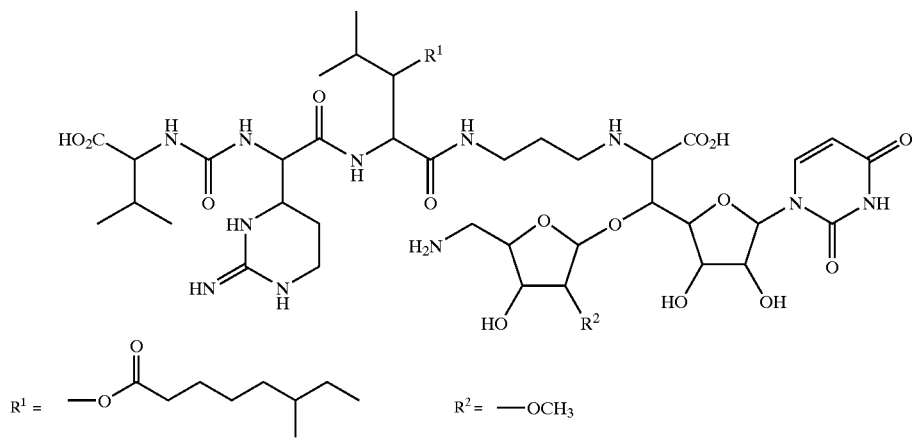
or pharmaceutically acceptable salts thereof.
7. The compound AA-896-B4 which has the structure:
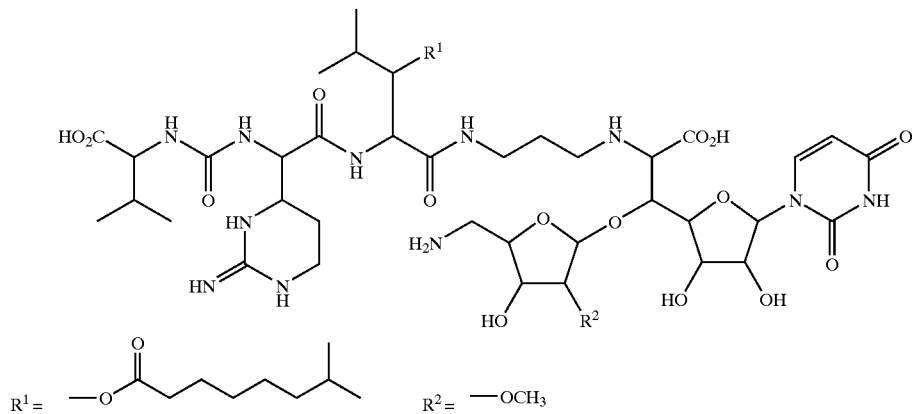
or pharmaceutically acceptable salts thereof.

8. The compound AA-896-A4 which has the structure:
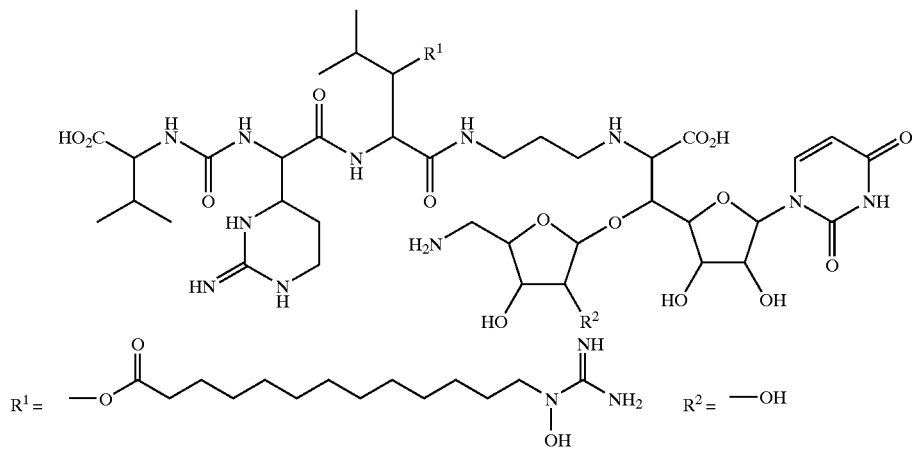
or pharmaceutically acceptable salts thereof.
9. The compound AA-896-C2 which has the structure:
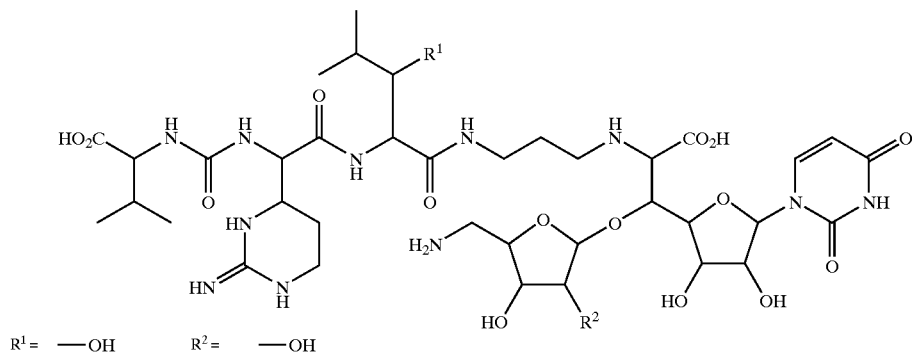
or pharmaceutically acceptable salts thereof.
10. The compound AA-896-C1 which has the structure:
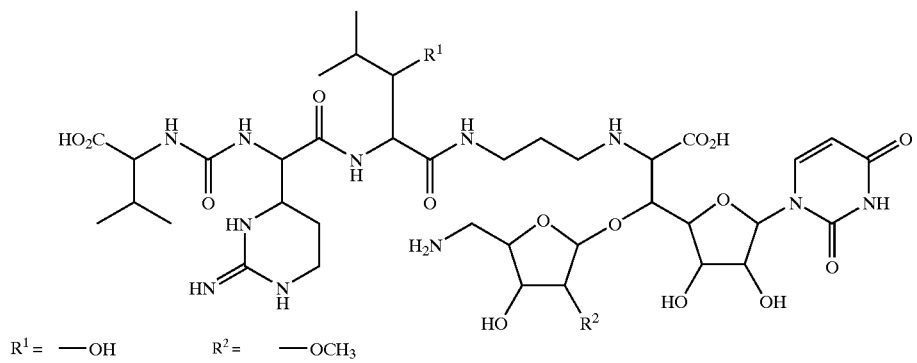
or pharmaceutically acceptable salts thereof.

11. The compound AA-896-D2 which has the structure:
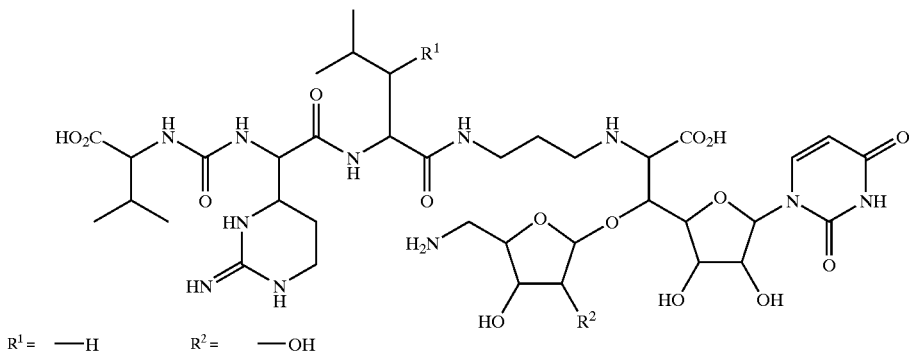
$R^1 = $ —H    $R^2 = $ —OH
or pharmaceutically acceptable salts thereof.
12. The compound AA-896-D3 which has the structure:
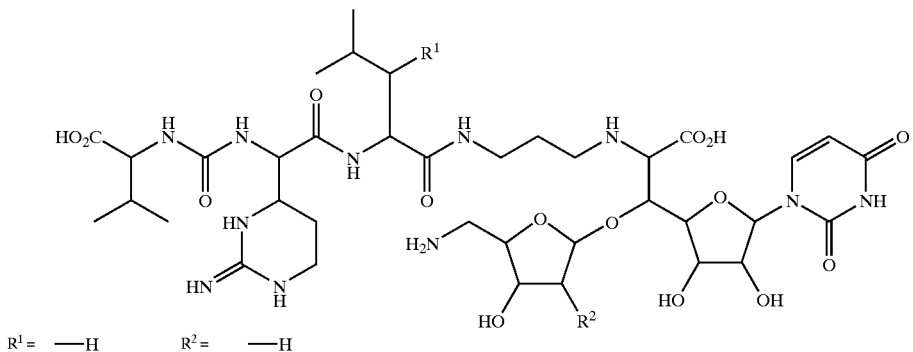
$R^1 = $ —H    $R^2 = $ —H
or pharmaceutically acceptable salts thereof.
13. The compound AA-896-D1 which has the structure:
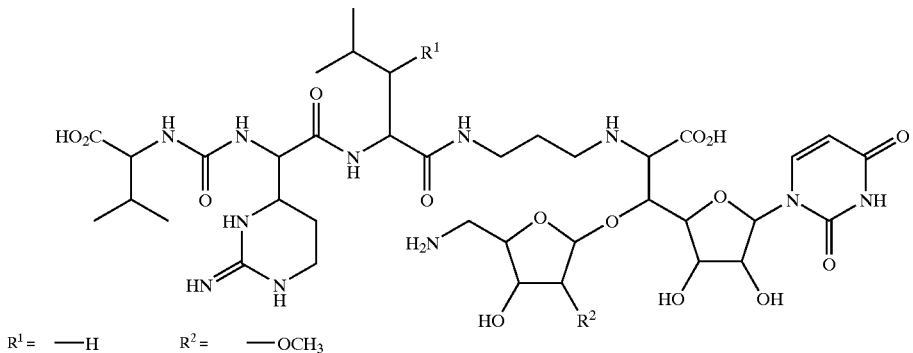
$R^1 = $ —H    $R^2 = $ —OCH$_3$
or pharmaceutically acceptable salts thereof.

14. The compound AA-896-A3 which has the structure:
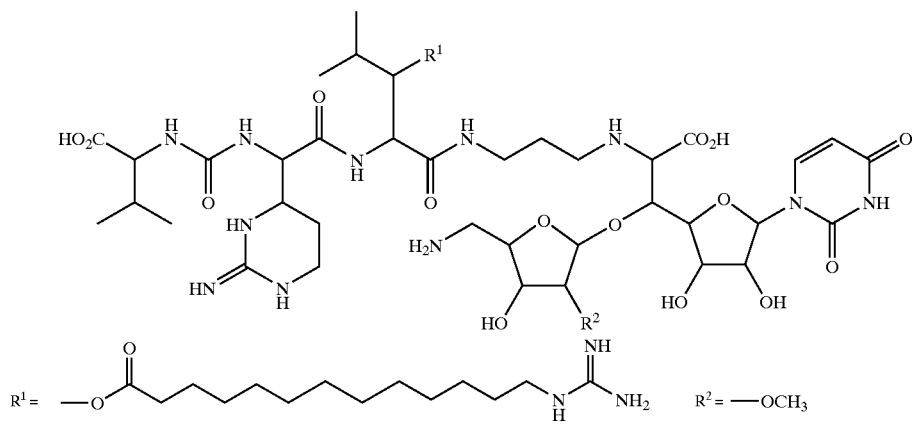
or pharmaceutically acceptable salts thereof.
15. The compound AA-896-C3 which has the structure:
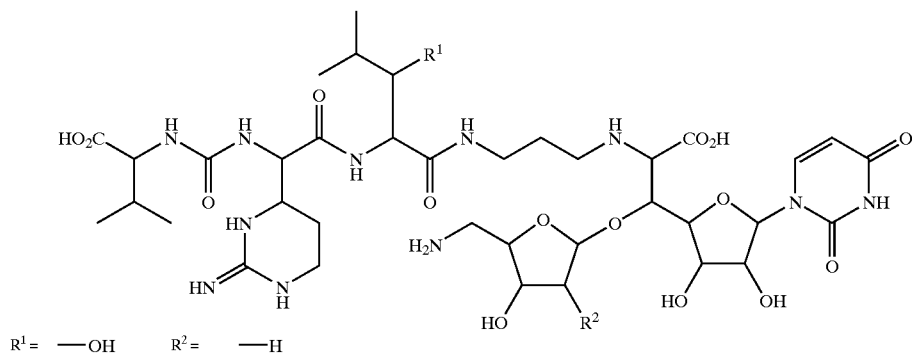
or pharmaceutically acceptable salts thereof.
16. The compound AA-896-B7 which has the structure:
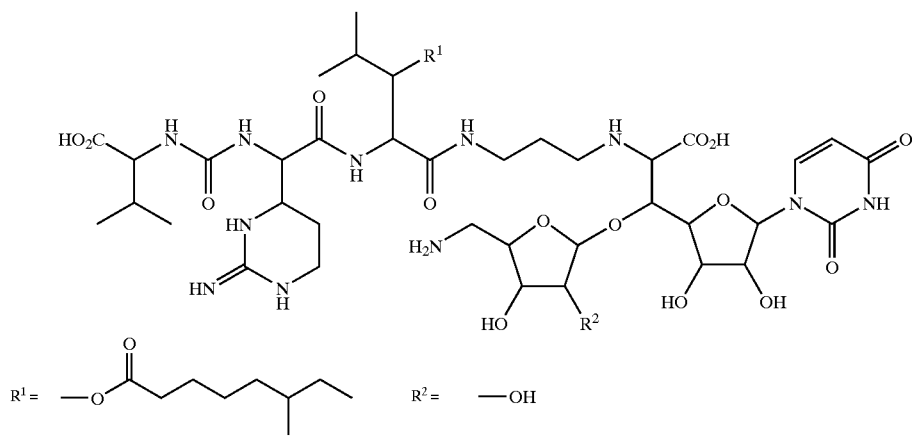
or pharmaceutically acceptable salts thereof.

17. The compound AA-896-B6 which has the structure:
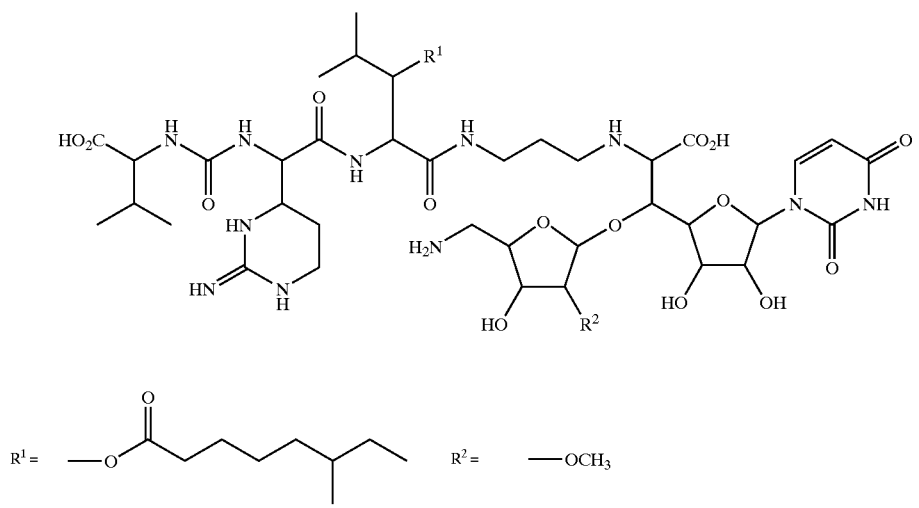
or pharmaceutically acceptable salts thereof.
18. The compound AA-896-C4 which has the structure:
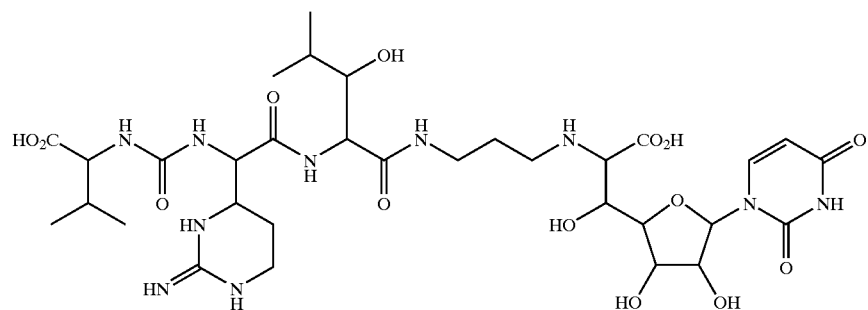
or pharmaceutically acceptable salts thereof.
19. The compound AA-896-A5 which has the structure:
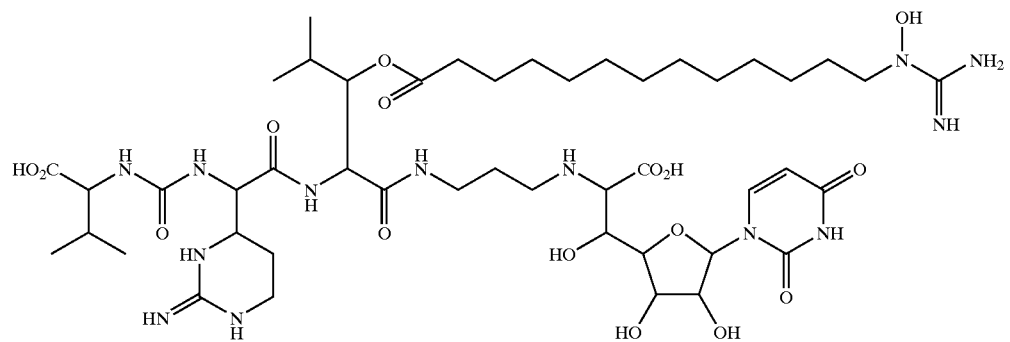
or pharmaceutically acceptable salts thereof.

20. The compound AA-896-C5 which has the structure:
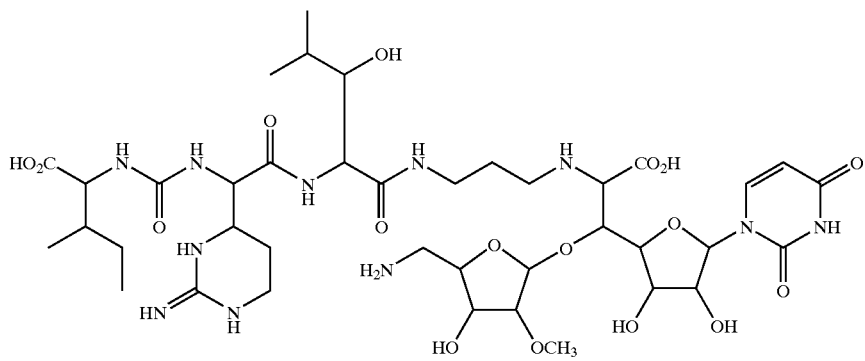
or pharmaceutically acceptable salts thereof.
21. The compound AA-896-D4 which has the structure:
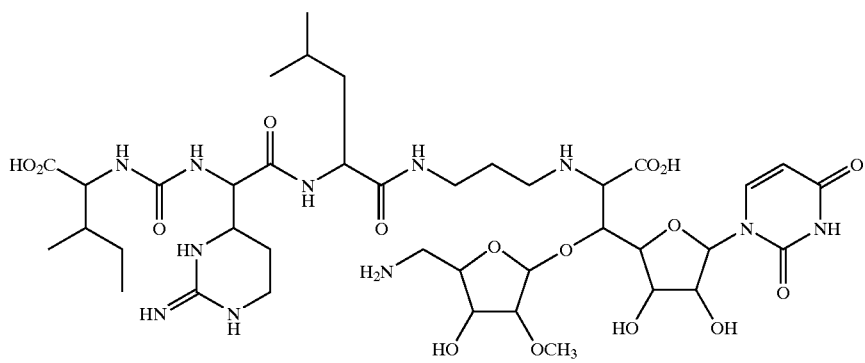
or pharmaceutically acceptable salts thereof.
22. The compound AA-896-A6 which has the structure:
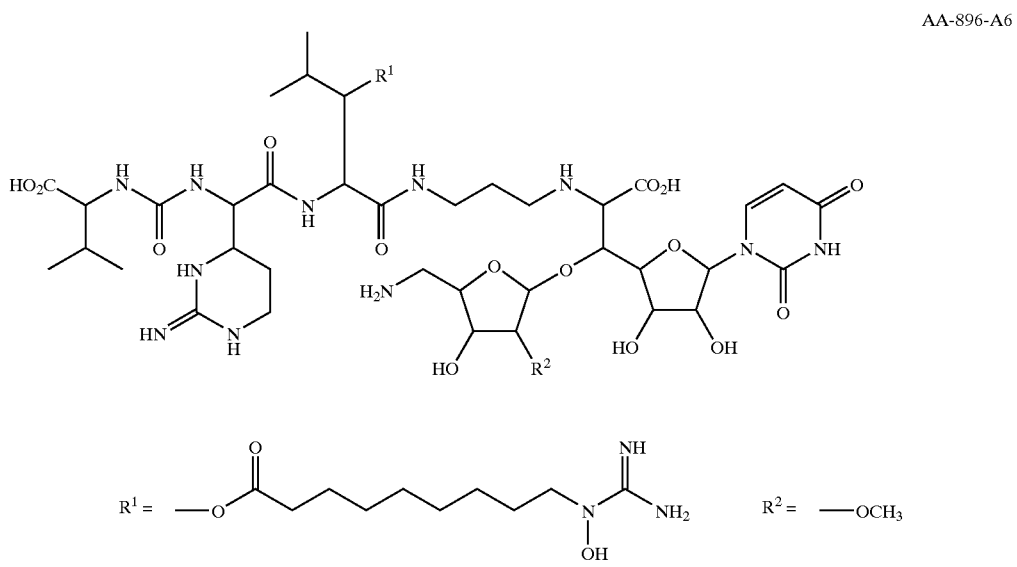
or pharmaceutically acceptable salts thereof.

23. A method for the prevention, treatment or control of bacterial infections in warm-blooded animals which comprises providing to said warm-blooded animal a antibacterially effective amount of the compound according to claim 1 or a pharmaceutically acceptable salt thereof.

24. A pharmaceutical composition comprising the compound according to claim 1 in association with a pharmaceutically acceptable carrier.

25. A method for the prevention, treatment or control of bacterial infections in warm-blooded animals which comprises providing to said warm-blooded animal a antibacterially effective amount of the compound according to claim 2 or a pharmaceutically acceptable salt thereof.

26. A pharmaceutical composition comprising the compound according to claim 2 in association with a pharmaceutically acceptable carrier.

27. A method for the prevention, treatment or control of bacterial infections in warm-blooded animals which comprises providing to said warm-blooded animal a antibacterially effective amount of the compound according to claim 3 or a pharmaceutically acceptable salt thereof.

28. A pharmaceutical composition comprising the compound according to claim 3 in association with a pharmaceutically acceptable carrier.

29. A method for the prevention, treatment or control of bacterial infections in warm-blooded animals which comprises providing to said warm-blooded animal a antibacterially effective amount of the compound according to claim 4 or a pharmaceutically acceptable salt thereof.

30. A pharmaceutical composition comprising the compound according to claim 4 in association with a pharmaceutically acceptable carrier.

31. A method for the prevention, treatment or control of bacterial infections in warm-blooded animals which comprises providing to said warm-blooded animal a antibacterially effective amount of the compound according to claim 5 or a pharmaceutically acceptable salt thereof.

32. A pharmaceutical composition comprising the compound according to claim 5 in association with a pharmaceutically acceptable carrier.

33. A method for the prevention, treatment or control of bacterial infections in warm-blooded animals which comprises providing to said warm-blooded animal a antibacterially effective amount of the compound according to claim 6 or a pharmaceutically acceptable salt thereof.

34. A pharmaceutical composition comprising the compound according to claim 6 in association with a pharmaceutically acceptable carrier.

35. A method for the prevention, treatment or control of bacterial infections in warm-blooded animals which comprises providing to said warm-blooded animal a antibacterially effective amount of the compound according to claim 7 or a pharmaceutically acceptable salt thereof.

36. A pharmaceutical composition comprising the compound according to claim 7 in association with a pharmaceutically acceptable carrier.

37. A method for the prevention, treatment or control of bacterial infections in warm-blooded animals which comprises providing to said warm-blooded animal a antibacterially effective amount of the compound according to claim 8 or a pharmaceutically acceptable salt thereof.

38. A pharmaceutical composition comprising the compound according to claim 8 in association with a pharmaceutically acceptable carrier.

39. A method for the prevention, treatment or control of bacterial infections in warm-blooded animals which comprises providing to said warm-blooded animal a antibacterially effective amount of the compound according to claim 9 or a pharmaceutically acceptable salt thereof.

40. A pharmaceutical composition comprising the compound according to claim 9 in association with a pharmaceutically acceptable carrier.

41. A method for the prevention, treatment or control of bacterial infections in warm-blooded animals which comprises providing to said warm-blooded animal a antibacterially effective amount of the compound according to claim 10 or a pharmaceutically acceptable salt thereof.

42. A pharmaceutical composition comprising the compound according to claim 10 in association with a pharmaceutically acceptable carrier.

43. A method for the prevention, treatment or control of bacterial infections in warm-blooded animals which comprises providing to said warm-blooded animal a antibacterially effective amount of the compound according to claim 11 or a pharmaceutically acceptable salt thereof.

44. A pharmaceutical composition comprising the compound according to claim 11 in association with a pharmaceutically acceptable carrier.

45. A method for the prevention, treatment or control of bacterial infections in warm-blooded animals which comprises providing to said warm-blooded animal a antibacterially effective amount of the compound according to claim 12 or a pharmaceutically acceptable salt thereof.

46. A pharmaceutical composition comprising the compound according to claim 12 in association with a pharmaceutically acceptable carrier.

47. A method for the prevention, treatment or control of bacterial infections in warm-blooded animals which comprises providing to said warm-blooded animal a antibacterially effective amount of the compound according to claim 13 or a pharmaceutically acceptable salt thereof.

48. A pharmaceutical composition comprising the compound according to claim 13 in association with a pharmaceutically acceptable carrier.

49. A method for the prevention, treatment or control of bacterial infections in warm-blooded animals which comprises providing to said warm-blooded animal a antibacterially effective amount of the compound according to claim 14 or a pharmaceutically acceptable salt thereof.

50. A pharmaceutical composition comprising the compound according to claim 14 in association with a pharmaceutically acceptable carrier.

51. A method for the prevention, treatment or control of bacterial infections in warm-blooded animals which comprises providing to said warm-blooded animal a antibacterially effective amount of the compound according to claim 15 or a pharmaceutically acceptable salt thereof.

52. A pharmaceutical composition comprising the compound according to claim 15 in association with a pharmaceutically acceptable carrier.

53. A method for the prevention, treatment or control of bacterial infections in warm-blooded animals which comprises providing to said warm-blooded animal a antibacterially effective amount of the compound according to claim 16 or a pharmaceutically acceptable salt thereof.

54. A pharmaceutical composition comprising the compound according to claim 16 in association with a pharmaceutically acceptable carrier.

55. A method for the prevention, treatment or control of bacterial infections in warm-blooded animals which comprises providing to said warm-blooded animal a antibacterially effective amount of the compound according to claim 17 or a pharmaceutically acceptable salt thereof.

56. A pharmaceutical composition comprising the compound according to claim 17 in association with a pharmaceutically acceptable carrier.

57. A method for the prevention, treatment or control of bacterial infections in warm-blooded animals which comprises providing to said warm-blooded animal a antibacterially effective amount of the compound according to claim 18 or a pharmaceutically acceptable salt thereof.

58. A pharmaceutical composition comprising the compound according to claim 18 in association with a pharmaceutically acceptable carrier.

59. A method for the prevention, treatment or control of bacterial infections in warm-blooded animals which comprises providing to said warm-blooded animal a antibacterially effective amount of the compound according to claim 19 or a pharmaceutically acceptable salt thereof.

60. A pharmaceutical composition comprising the compound according to claim 19 in association with a pharmaceutically acceptable carrier.

61. A method for the prevention, treatment or control of bacterial infections in warm-blooded animals which comprises providing to said warm-blooded animal a antibacterially effective amount of the compound according to claim 20 or a pharmaceutically acceptable salt thereof.

62. A pharmaceutical composition comprising the compound according to claim 20 in association with a pharmaceutically acceptable carrier.

63. A method for the prevention, treatment or control of bacterial infections in warm-blooded animals which comprises providing to said warm-blooded animal a antibacterially effective amount of the compound according to claim 21 or a pharmaceutically acceptable salt thereof.

64. A pharmaceutical composition comprising the compound according to claim 21 in association with a pharmaceutically acceptable carrier.

65. A method for the prevention, treatment or control of bacterial infections in warm-blooded animals which comprises providing to said warm-blooded animal a antibacterially effective amount of the compound according to claim 22 or a pharmaceutically acceptable salt thereof.

66. A pharmaceutical composition comprising the compound according to claim 22 in association with a pharmaceutically acceptable carrier.

67. A compound of the formula:

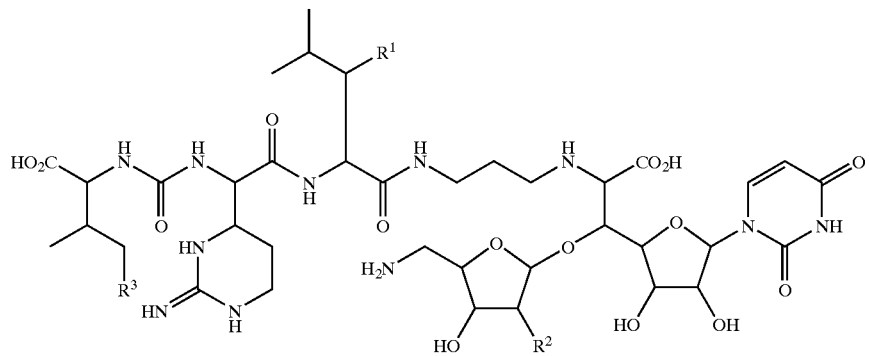

wherein:

$R^1$ is H or $R^4$;

$R^2$ is H, OH or $OCH_3$;

$R^3$ is H or $CH_3$;

$R^4$ is represented by the formula

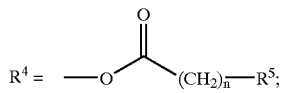

n is an integer from 4 to 12;

$R^5$ is straight and branched alkyl of 1 to 4 carbon atoms, carbamimidoylamino or carbamimidoylhydroxyamino; or a pharmaceutically acceptable salt thereof.

68. A method for the prevention, treatment or control of bacterial infections in warm-blooded animals which comprises providing to said warm-blooded animal a antibacterially effective amount of a compound according to claim 67 or a pharmaceutically acceptable salt thereof.

69. A pharmaceutical composition comprising an effective amount of a compound according to claim 62 in association with a pharmaceutically acceptable carrier.

* * * * *

UNITED STATES PATENT AND TRADEMARK OFFICE
CERTIFICATE OF CORRECTION

PATENT NO. : 6,689,763 B2
DATED : February 10, 2004
INVENTOR(S) : Guy Thomas Carter, Jason Arnold Lotvin and Leonard Alexander McDonald It is certified that error appears in the above-identified patent and that said Letters Patent is hereby corrected as shown below:

Column 14,
Line 54, "$C_{52}N_{90}N_{11}O_{18}$" and insert -- $C_{52}H_{90}N_{14}O_{18}$ -- therefore.

Column 31,
Line 39, delete the structure 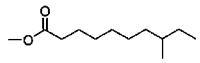

and insert the structure 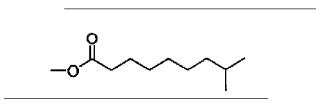

Column 39,
Line 60, delete the structure 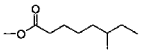

and insert the structure 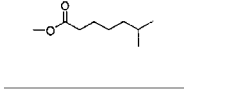

Column 41,
Line 20, delete this structure 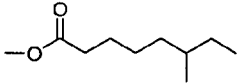

and insert the structure 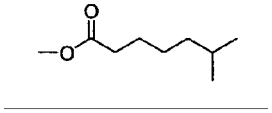

Signed and Sealed this

Twenty-fourth Day of August, 2004

JON W. DUDAS
*Director of the United States Patent and Trademark Office*